(12) United States Patent
Van Dyke

(10) Patent No.: US 7,001,988 B2
(45) Date of Patent: Feb. 21, 2006

(54) METHODS FOR CONTROLLING PEPTIDE SOLUBILITY, CHEMICALLY MODIFIED PEPTIDES, AND STABLE SOLVENT SYSTEMS FOR PRODUCING SAME

(75) Inventor: Mark Van Dyke, Fair Oaks Ranch, TX (US)

(73) Assignee: Keraplast Technologies, Ltd., San Antonio, TX (US)

( * ) Notice: Subject to any disclaimer, the term of this patent is extended or adjusted under 35 U.S.C. 154(b) by 519 days.

(21) Appl. No.: 10/254,364

(22) Filed: Sep. 25, 2002

(65) Prior Publication Data

US 2003/0119089 A1 Jun. 26, 2003

Related U.S. Application Data

(60) Provisional application No. 60/324,709, filed on Sep. 25, 2001.

(51) Int. Cl.
C07K 14/47 (2006.01)
(52) U.S. Cl. .................................. 530/357; 530/350
(58) Field of Classification Search ................ 530/350, 530/357
See application file for complete search history.

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 2,434,688 A | 1/1948 | Evans | |
| 3,250,682 A | 5/1966 | Wilmsmann et al. | |
| 3,642,498 A | 2/1972 | Anker | |
| 3,677,693 A | 7/1972 | Fillingham | |
| 3,842,848 A | 10/1974 | Karlala | |
| 4,041,150 A | 8/1977 | Karjala | |
| 4,279,996 A | 7/1981 | Yoshioka et al. | |
| 4,423,032 A | 12/1983 | Abe et al. | |
| 4,474,694 A | 10/1984 | Coco et al. | |
| 4,495,173 A | 1/1985 | Matsunaga et al. | |
| 4,504,644 A | 3/1985 | Lang et al. | |
| 4,570,629 A | 2/1986 | Widra | |
| 4,659,566 A | 4/1987 | Petrow | |
| 4,751,074 A | 6/1988 | Matsunaga et al. | |
| 4,895,722 A | 1/1990 | Abe et al. | |
| 4,906,460 A | 3/1990 | Kim et al. | |
| 4,959,213 A | 9/1990 | Brod et al. | |
| 5,047,249 A | 9/1991 | Rothman et al. | |
| 5,073,294 A | 12/1991 | Shannon et al. | |
| 5,202,053 A | 4/1993 | Shannon | |
| 5,219,562 A | 6/1993 | Fujiu et al. | |
| 5,258,501 A | 11/1993 | Barbaric et al. | |
| 5,276,138 A | 1/1994 | Yamada et al. | |
| 5,300,285 A | 4/1994 | Halloran et al. | |
| 5,356,433 A | 10/1994 | Rowland et al. | |
| 5,358,935 A | 10/1994 | Smith et al. | |
| 5,412,076 A | 5/1995 | Gagnieu | |
| 5,424,062 A | 6/1995 | Schwan et al. | |
| 5,425,937 A | 6/1995 | Uchiwa et al. | |
| 5,505,952 A | 4/1996 | Jiang et al. | |
| 5,520,925 A | 5/1996 | Maser | |
| 5,563,230 A | 10/1996 | Hsu et al. | |
| 5,654,471 A | 8/1997 | Zahn et al. | |
| 5,679,819 A | 10/1997 | Jones et al. | |
| 5,712,252 A | 1/1998 | Smith | |
| 5,833,880 A | 11/1998 | Siemensmeyer et al. | |
| 5,932,552 A | 8/1999 | Blanchard et al. | |
| 5,942,009 A | 8/1999 | Burns | |
| 5,948,432 A | 9/1999 | Timmons et al. | |
| 5,955,549 A | 9/1999 | Chang et al. | |
| 5,989,461 A | 11/1999 | Coates et al. | |
| 6,087,462 A | 7/2000 | Bowers et al. | |
| 6,090,308 A | 7/2000 | Coates et al. | |
| 6,110,487 A | 8/2000 | Timmons et al. | |
| 6,124,265 A | 9/2000 | Timmons et al. | |
| 6,159,495 A | 12/2000 | Timmons et al. | |
| 6,159,496 A | 12/2000 | Blanchard et al. | |
| 6,165,496 A | 12/2000 | Timmons et al. | |
| 6,211,296 B1 | 4/2001 | Frate et al. | |
| 6,270,791 B1 | 8/2001 | Van Dyke et al. | |
| 6,270,793 B1 | 8/2001 | Van Dyke et al. | |
| 6,274,155 B1 | 8/2001 | Van Dyke et al. | |
| 6,274,163 B1 | 8/2001 | Blanchard et al. | |
| 6,316,598 B1 | 11/2001 | Van Dyke et al. | |
| 6,352,699 B1 | 3/2002 | Mondet et al. | |
| 6,361,767 B1 | 3/2002 | Malle et al. | |
| 6,371,984 B1 | 4/2002 | Van Dyke et al. | |
| 6,379,690 B1 | 4/2002 | Blanchard et al. | |
| 6,399,051 B1 | 6/2002 | Dannecker et al. | |
| 6,432,435 B1 | 8/2002 | Timmons et al. | |
| 6,435,193 B1 | 8/2002 | Cannell et al. | |
| 6,461,628 B1 | 10/2002 | Blanchard et al. | |
| 2005/0054053 A1* | 3/2005 | Aguinaldo et al. | ...... 435/69.51 |

FOREIGN PATENT DOCUMENTS

| | | |
|---|---|---|
| EP | 0097907 | 1/1984 |
| EP | 0 298 684 A3 | 1/1989 |
| EP | 0454 6000 A1 | 10/1991 |

(Continued)

OTHER PUBLICATIONS

Croda, Ltd., Keratec Pep, DC138_Pep_Datasheet, Apr. 13, 2004.*
S. F. Sadova and A. A. Konkin, Grafting of vinyl monomers onto wool keratin in an oxidation-reduction system. Zh Vses Khim O-va 1967; 12(5): 596-7.

(Continued)

Primary Examiner—Robert A. Wax
(74) Attorney, Agent, or Firm—Vinson & Elkins L.L.P.

(57) ABSTRACT

Methods for chemically modifying peptides, preferably keratinaceous feedstocks, to achieve desired solubility characteristics; stable solvent systems for preparing the modified peptides; and, the resulting chemically modified peptides.

97 Claims, No Drawings

FOREIGN PATENT DOCUMENTS

| | | |
|---|---|---|
| EP | 0 468 797 A2 | 1/1992 |
| EP | 0540357 | 5/1993 |
| JP | 57-23631 * | 2/1982 |
| JP | 4-189833 | 7/1992 |
| JP | 2002-113815 | 4/2002 |
| WO | WO 93/10827 | 6/1993 |
| WO | WO 93/22397 | 11/1993 |
| WO | WO 98/08550 | 3/1995 |
| WO | WO 9931167 | 6/1999 |
| WO | WO 03008006 | 1/2003 |

OTHER PUBLICATIONS

Iwata, et al.; Coating Film For Living Tissues; Nov. 2, 1985; total of 9 pages; Japanese Patent Application Kokai Publication No. Sho 60-220068.

Endo; De-Allergenized Rubber of Plastic Molding Used in the Field of Medicla Care; Apr. 16, 2002; total of 5 pages; Japanese Patent Application Kokai Publication No. 2002-113815.

Yoshioka et al; Modified Animal Hair or Wool Powder, Jul. 11, 1989; total of 13 pages; Japanese Unexamined Patent Application Publication H01-174528.

Miyamoto et al; Process for Producing Modified Keratin Protein; Feb. 6, 1982; total of 4 pages; Japanese Patent Application Kokai Publication No. Sho 57-23631.

Yamauchi et al; Karatin Microcapsule, Production of Keratin Microcapsule, and Cosmetics containing Keratin Microcapsules; Dec. 22, 1998; total of 5 pages; japanes Patent Application Kokai Publication No. H10-3337466.

J.M. Gillespie, et al., "Amino Acid composition of a Sulphur-rich Protein Wool," Biochim. Biophy. ACTA, (1960) pp. 538-539; vol. 39.

Keith H. Gough, et al., "Amino Acid Sequence of alpha - Helical Segments from S-Carboxymethylkerateine-A: Complete Sequence of a Type-I Segment," Biochem. J. (1978), pp. 373-385; vol. 173.

Thomas C. Elleman, et al., "Amino Acod Sequemces pf alpha -Helical Segments from S-Carboxymethylkerateine-A:. Statistical Analysis," Biochem. J. (1978), pp. 387-391, vol. 173.

David McC. Hogg, et al., "Amino Acid Sequences of alpha-Helical Segments from S-Carboxymethlkerateine-:. Tryptic and Chymotryptic Peptides from a Type-II Segment," Biochem. J. (1978), pp. 353-363; vol. 173.

W. Gordon Crewther, et al., "Amino Acid Sequences of alpha -Helical Segments from S-Carboxymethylkerateine-A: Complete Sequence of a Type-II Segment," Biochem. J. (1978), pp. 405-411. vol. 22.

C. Earland, et al., "Studies on the Structure of Karatin: II. The Amino Acid Context of Fractions Isolated from Oxidized Wool," Biochemica Et Biophysica Acta (1956), pp. 405-411. vol. 22.

J.M. Gillespie, et al., "Preparation of an Electrophoretically Homogeneous Keratin Derivative from Wool," Short Communications, Preliminary Notes, (1953), pp. 481-482, vol. 12.

Maurice J. Frenkel, et al., "The Isolation and Properties of a Tyrosine-Rich Protein from Wool: component 0.62," Eur. J. Biochem, (1973) pp. 112-119, vol. 34.

R.J. Blagrove, et al., "The Electrophoresis of the High-Tyrosine Proteins of Keratins on Cellulose Acetate Strips," Comp. Biochem. Physiol., (1975) pp. 571-572, vol. 50B.

Robert C. Marshall, et al., "Successful Isoelectric Focusing of Wool Low-Sulphur Proteins," Journal of Chromatography, (1979) pp. 351-356, vol. 172.

Robert C. Marshall, "Characterization of the Proteins of Human Hair and Nail by Electrophoresis," The Journal of Investigation Dermatology, (1983) pp. 519-524, vol. 80.

W. G. Crewther, et al. "Helix-Rich Fraction from Low-Sulphur Proteins of Wool," Nature, (Jul. 17, 1965) p. 295, No. 4994.

H. Lindley, et al., "Occurrence of the Cys-Cys Sequence in Keratins," J. Mol. Biol., (1967) pp. 63-67, vol. 30.

Robert C. Marshall, "Genetic Variation in the Proteins of Human Nail," The Journal of Investigate Dermatology, (1980) pp. 264-269, vol. 75.

M. E. Campbell, et al., "Compositional Studies of High-and Low-Crimp Wools," Aust. J. Biol. Sci., (1972) pp. 977-1087, vol. 25.

P.J Reis, et al. "A Relationship between Sulphur Content of Wool and Wool Production by Merino Sheep,"0 Aust. J. Biol. Sci., (1967) pp. 153-163, vol. 20.

Robert C. Marshall, et al., "The Keratin Proteins of Wool, Horn and Hoof from Sheep," Aust. J. Biol. Sci, (1977) pp. 389-400, vol. 30.

J.M. Gillespie. "Reaction of Sodium Borohydride with Wool," nature, (Jan. 31, 1959) pp. 322-323, vol. 183.

David R. Goddard, et al., "A Study on Keratin," J. Bio. Chem., (1934) pp. 605-614, vol. 106.

L.M. Dowlling, et al., "Isolation of Components from the Low-Sulphur Proteins of Wool By Fractional Preciptation Preparative Biochemistry," (1974) pp. 203-226, vol. 4 (3).

W.G. Crewther, et al., "Reduction of S-Carboxymethylcysteine and Methionine with Sodium in Liquid Ammonia," Biochim. Biophys. Acta, (1969) pp. 609-611, vol. 164.

W.T. Agar, et al., "The Isolation from Wool of a Readily Extractable Protein of Low Sulphur Content," Biochim. Biophys Acta, (1958) pp. 225-226, vol. 27.

H. Lindley, et al., "The Reactivity of the Disulphide Bonds of Wool," Biochem J. (1974) pp. 515-523, vol. 139.

M. Schornig, et al., "Synthesis of Nerve Growth Fractor mRNA in CUltures of Developing Mouse Whisker Pad, A Peripheral Target Tissue of Sensory Trigeminal Neurons," The Journal of Cell Biology, (Mar. 1993) pp. 1471-1479, vol. 120, No. 6.

S. Mitsui, et al., "Genes for a Range of Growth Factors and Cyclin-Dependent Kinase Inhibitors are Expressed by Isolated Human Hair Follicles," British Journal of Dermatology (1997) pp. 693-698, vol. 137.

B. K. Flishie, et al., "The Fine Structure of alpha -keratin," J. Mol. Biol. (1961) pp. 784-786, vol.3.

R.D.B. Fraser, et al., "Structure of alpha -Keratin," nature, (Feb. 28, 1959) pp. 592-594, vol. 183.

R.D.B. Fraser, et al. "Helical Models of Feather Keratin Structure," Nature, (Sep. 22, 1962) pp. 1167-1168, vol. 195.

B.K. Filshie, et al., "An Electron Microscope Study of the fine Structure of Feather Keratin," The Journal of Cell Biology (1962) pp. 1-12, vol. 13.

W.G. Crewther, et al., "Low-Sulfur Proteins from alpha - Keratins. Interrelationships between their Amino Acid Compositions, alpha-Helix Contents, and the Supercontraction of the Parent keratin," Biopolymers (1966) pp. 905-916, vol. 4.

G. M. Bhatnagar, et al., "The Conformation of the High-Sulphur Proteins of Wool. I. The Preparation and Properties of a Water-Sulphur Metakeratin," Int. J. Protein Research I. (1969), pp. 199-212.

W.G. Crewther, et al., "The Preparation and Properties of a Helix-Rich Fraction obtained by partial Proteolysis of Low Suplhur S-Carboxymethlkerateine from Wool," (1967) the Journal of Biological Chemistry (Issue of Oct. 10), pp. 4310-4319, vol. 242, No. 19.

D.A.D. Parry, et al., "Structure of alpha -Keratin: Structural Implication of the Amino Acid Sequences of th Type I and II Chain Segments," J. Mol. Biol. (1977) pp. 449-454, vol. 113.

E. Suzuki, et al., "X-Ray Diffraction and Infrared Studies of an aplpha-Helical Fragment from alpha -Keratin," J. MolL. Biol. (1973) pp. 275-278, vol. 73.

G.M. Bhatnagar, et al., "The Conformation of the High-Sulphur Proteins of Wool: II. Difference Spectra of Kerateine-b," In. J. ResearchI, (1969) pp. 213-219.

Dean R. Heewish, et al., "In Vitro Growth and Differentiationof Epithelial Cells Derived from Post-Embryonic Hair Follicles," Aust. J. Biol. Sci., (1982) pp. 103-109, vol. 35.

A.M. Downes, et al., "A Study of the Proteins of the Wool Follicle," Aust. J. Biol. Sci., (1966) pp. 319-333, vol. 19.

G.E. Rogers, et al., "Keratin Protofilaments and Ribsomes from Hair Follicles," Nature, (Jan. 2, 1965), pp. 77-78, vol. 205.

P.M. Steinert et al., "In Vitro Studies on the synthesis of Guinea Pig Hair Keratin Proteins," Biochimica et Biophysica Acta, (1958) pp. 33-43, vol. 29.

G.E. Rogers, et al., "Some Observations on the Proteins of the Inner Root Sheath Cells of Hair Follicles," Biochemica et Biophysica Acta, (1958) pp. 33-43, vol. 29.

Leslie N. Jones, et al., "Studies of Developing Human Hair Shaft Cells in Vitro," The Journal of Investigative Dermatology., (jan. 1988) pp. 58-64, vol. 90.

Trevor Jarman, et al., "Prospects for Novel Biomaterials Development," Online Publications, Pinner, Uk, Presented at Biotech '85 (Europe)(1985) pp. 505-512.

Akira Tachibana, et al., "Fabrication of Wool Keratins Sponge Scaffolds for Long-Term Cells Cultivation," Journal of Biotechnology, (2002) pp. 165-170, vol. 93.

J.M. Gillispie, et al., "Periodicity in High-sulphur Proteins from Wool," Nature, (Sep. 18, 1965) pp. 530-531, vol. 246.

Kiyoshi Yamauchi, "The Development of Keratin: Characteristics of Polymer Films," [Research Report]; pp. 1-12.

"Scattering to Structural Foams, Skin, Synthetic" Encyclopedia of Polymer and Science and Engineering, (1989) pp. 335-345, vol. 15.

J. M. Gillespie, et al., "Proteins Rich in Glycine and Tyrosine from Keratins," Comp. Biochem. Physiol., (1972) pp. 723-734, vol. 41B.

R.D.B. Fraser, et al., "Tyrosine-Rich Proteins in Keratins," Comp. Biochem. Physiol., (1973) pp. 943-947, vol.. 44B.

J.M. Gillespie, et al., "Relation Between the Tyrosine Content of Various Wools and their Content of a Class of Proteins Rich in Tyrosine Content and Glycine," Aust. J. Biol. Sci., (1971) pp. 1189-1197, vol. 24.

J. M. Gillespie, et al., "The Macroheterogeneity of Type I Tyrosine-rich Proteins of Merino Wool," Aust. J. Biol. Sci., (1974) pp. 617-627, vol. 27.

E.G. Bendit, et al., "The Probable Role and Location of High-Glycine-Tyrosine Proteins in the Structure of Keratins," BIOPOLYMERS, (1978) pp. 2743-2745, vol. 17.

Robert C. Marshall, et al. "High-Sulphur Proteins from alpha -Keratins: 11. * Isolation and Partial Characterization of Purified Components from Mouse Hair," Aust. J. Biol. Sci. (1976) pp. 11-20, vol. 29.

Robert C. Marshall, et al. "High-Sulphur Proteins from alpha -Keratins: 1. Heterogeneity of the Proteins from Mouse Hair," Aust. J. Biol. Sci. (1976) pp. 1-10, vol. 29.

R. L. Darskus, et al. "The Possibillity of Common Amino Acid Sequences in High-Sulphur Protein Fractions From Wool," Aust. J. Biol. Sci. (1969) pp. 1197-1204, vol. 22.

Robert C. Marshall, et al. "Heterogeneity and Incomplete DIsulfide Reduction in the High-Sulfur Proteins of Wool," Aust. J. Biol. Sci. (1978) pp. 219-229, vol. 31.

H. Lindley, et al., "The Preparation and Properties of a Group of Proteins from the High-Sulphur Fraction of Wool," Biochem. J. (1972) pp. 859-867, vol. 128.

J.M. Gillespie, et al., "Evidence of Homology in a High-Sulphur Protein Fraction (SCMK-B2) of Wool and Hair alpha -Keratins," Biochem. J. (1968) pp. 193-198, vol. 110.

J. M. Gillespie, et al., "A Comparative Study of High-Sulphur Proteins from alpha-Keratins," Comp. Biochem. Physiol. (1965) pp. 175-185, vol. 15.

J. M. Gillespie, et al., "High-Sulphur Proteins as a Major Cuase of Variation in Sulphur Content Between alpha -Keratins," Nature (Sep. 18,1965) pp. 1293-1294, vol. 207.

R. D. B. Fraser, et al., "Molecular Organization in Alpha-Keratin," Nature, (Mar. 17, 1962) pp. 1052-1055, vol. 193.

Dr. P. Alexander, et al., "Structure of Wool Fibres," Nature, (Sep. 2, 1950) pp. 396-398.

Node, et al., "Hard Acid and Soft Nuclepphile System. 2. Demethylation of Methyl Ethers of Alcohol and Phenol with an Aluminum Halide-Thiol System," J. Org. Chem (1980), pp. 4275-4277. vol. 45.

Ito, et al., "Biocompatibility of Denatured Wool Keratin, " Konbushi Ronbunshu [Collected Essays on Polymers], (Apr. 1982) pp. 249-256, vol. 39, No. 4.

Tatsuya and Ishii, "Keratin Protein High Pressure Molded Article,";Japanese Patent Application, (Dec. 03, 1993), total of six pages, Public Patent Annoucement 1993-320358.

Saeki, Yokogawa, and Ushara, "Production Method For Water-soluble Keratin Protein," Japanese Patent Application, (Feb. 21, 1990), total of five pages, Public Patent Announcement 1990-51533.

Miyamoto and Tsushima, "A Method for Preparing a Keratin Substance with a Low molecular Weight," Japanese Patent Application, (Jul. 8, 1982), total of five pages; Public Patent Disclosure Bulletin S57-109797.

R. D. B. Fraser, "The Chain Configuration of Wool Keratin," Short Communications, Preliminary Notes, (1953) pp. 482-483, vol. 12.

R. D. B. Fraser, et al., "Microscopic Observations of the Alkaline-Thioglycollate Extraction of Wool," Short Communications, Preliminary Notes, (1953) pp. 484, vol. 12.

Van Dyke mark et al., Development of keratin coatings for osteoinduction on titanium, , Abstracts of Papers American Chemical Society, vol. 224, No. 1-2, Aug. 18-22, 2002.

Tanaka, Yoshio et al., Reaction of Wool Keratin with Epoxides, Proceedings International Wo;;textil-Forschungskonf, vol. 3, 1976, pp. 192-201.

Fraenkel-Conrat, H., The Action of 1, 2-Epoxides on Proteins, Journal of Biological Chemistry, vol. 154, No. 1, Jun. 1, 1944.

Weetall HH.; Preparation of immobilized proteins covalently coupled through silane coupling agents to inorganic supports; Applied Biochemistry and Biotechnology; 1993; 157-188; 41(3).

Weetall, HH.; Preparationof immobilized proteins covalently coupled through silane coupling agents to inorganic supports; Advances in Molecular and Cell Biology; 1996; 161-192; 15A.

* cited by examiner

METHODS FOR CONTROLLING PEPTIDE SOLUBILITY, CHEMICALLY MODIFIED PEPTIDES, AND STABLE SOLVENT SYSTEMS FOR PRODUCING SAME

The present application claims the benefit of the filing date of U.S. Provisional Application 60/324,709, filed Sep. 25, 2001, now abandoned.

CROSS-REFERENCE TO RELATED APPLICATIONS

The present application is related to the following pending applications: U.S. patent application Ser. No. 10/133,885, filed Apr. 26, 2002, which is a continuation-in-part of copending U.S. patent application Ser. No. 10/119,477, filed Apr. 10, 2002; and U.S. patent application Ser. No. 10/127,523, filed Apr. 22, 2002. The present application is also related to the following provisional applications: U.S. Provisional Application No. 60/200,543, filed Apr. 27, 2000; U.S. Provisional Application No. 60/225,517, filed Aug. 15, 2000; U.S. Provisional Application No. 60/393,958, filed Jul. 5, 2002; and U.S. Provisional Application No. 60/399,039, filed Jul. 25, 2002.

FIELD OF THE APPLICATION

The application relates to methods for chemically modifying peptides to achieve desired solubility characteristics; to the chemically modified peptides, themselves; and, to stable solvent systems for preparing the chemically modified peptides. The peptides preferably are keratinaceous.

BACKGROUND OF THE APPLICATION

Keratin peptides, particularly water soluble keratin peptides, are beneficial in healing damaged epithelial tissues. Unfortunately, the chemical and engineering properties of water soluble keratin peptides have been relatively limited to those achieved using oxidative and reductive chemistries. A need exists for soluble keratin peptides with a broad scope of chemical and engineering properties so that the potential applications of keratin-based materials can be expanded. Methods for chemical modification of keratin peptides are especially needed to impart desired solubility properties to the keratin peptides while maintaining the healing activity of these compounds.

SUMMARY OF THE APPLICATION

A method for controlling solubility characteristics of a proteinaceous feedstock, said method comprising:
  providing said proteinaceous feedstock comprising primary reactive sites and secondary reactive sites;
  treating said feedstock to convert at least a fraction of said primary reactive sites to an ionic fraction, producing an ionic proteinaceous feedstock; and
  chemically modifying at least a portion of functionalities selected from the group consisting of unreacted primary reactive sites and secondary reactive sites, thereby producing a modified proteinaceous feedstock comprising a polar fraction at a ratio to said ionic fraction; and
  controlling said ratio to achieve solubility characteristics comprising an isoelectric band compatible with a selected solvent.

In another aspect, the application provides a method for controlling solubility characteristics of a proteinaceous feedstock, said method comprising:
  providing a proteinaceous feedstock comprising primary reactive sites and secondary reactive sites, said primary reactive sites being selected from the group consisting of cystine groups and cysteine groups;
  treating said feedstock to convert at least a fraction of said primary reactive sites to an ionic fraction, producing an ionic proteinaceous feedstock; and
  chemically modifying at least a portion of functionalities selected from the group consisting of unreacted primary reactive sites and secondary reactive sites selected from the group consisting of carboxylic acid groups, amine groups, and hydroxyl groups, thereby producing a modified proteinaceous feedstock comprising a polar fraction at a ratio to said ionic fraction; and
  controlling said ratio to achieve an isoelectric band compatible with a selected solvent.

In another aspect, the application provides a method for controlling solubility characteristics of a keratinaceous feedstock, said method comprising:
  providing a keratinaceous feedstock comprising primary reactive sites and secondary reactive sites, said primary reactive sites being selected from the group consisting of cystine groups and cysteine groups;
  treating said feedstock to convert at least a fraction of said primary reactive sites to an ionic fraction, producing an ionic keratinaceous feedstock; and
  chemically modifying at least a portion of functionalities selected from the group consisting of unreacted primary reactive sites and secondary reactive sites selected from the group consisting of carboxylic acid groups, amine groups, and hydroxyl groups, thereby producing a modified keratinaceous feedstock comprising a polar fraction at a ratio to said ionic fraction; and
  controlling said ratio to achieve an isoelectric band compatible with a selected solvent.

In another aspect, the application provides modified peptides comprising chemically modified functionalities selected from the group consisting of primary reactive sites and secondary reactive sites comprising a polar fraction at a ratio to an ionic fraction.

In another aspect, the application provides a stable solution comprising a mutual solvent comprising one or more dissolved hydrophobic reactant(s) having a first solubility parameter and ionic proteinaceous feedstock adapted to have a second solubility parameter substantially the same as said first solubility parameter.

In yet another aspect, the application provides a stable solution comprising a mutual solvent comprising one or more dissolved hydrophobic reactant(s) having a first solubility parameter and ionic keratin feedstock adapted to have a second solubility parameter substantially the same as said first solubility parameter.

In another aspect, the application provides a stable solvent system comprising:
  ionic proteinaceous feedstock dissolved in a first solvent, said ionic proteinaceous feedstock comprising an ionic fraction; and
  one or more hydrophobic reactant(s) dissolved in a second solvent that is miscible with said first solvent.

In another aspect, the application provides a stable solvent system comprising:
  ionic keratinaceous feedstock dissolved in a first solvent, said ionic keratinaceous feedstock comprising an ionic fraction; and, one or more hydrophobic reactants dissolved in a second solvent that is miscible with said first solvent.

In another aspect, the application provides a stable solvent system comprising:

ionic keratinaceous feedstock dissolved in a first solvent, said ionic keratinaceous feedstock comprising an ionic fraction; and, one or more organic reactants dissolved in a second solvent that is miscible with said first solvent.

In another aspect, the application provides a stable suspension comprising one or more hydrophobic reactant(s) comprising a second solvent suspended in a first solvent comprising ionic proteinaceous feedstock comprising an ionic fraction, wherein said second solvent is immiscible with said first solvent.

In yet another aspect, the application provides a stable suspension comprising an ionic keratinaceous feedstock suspended a first solvent, said stable suspension further comprising one or more dissolved hydrophobic reactant(s) comprising a second solvent, wherein said first solvent is immiscible with said second solvent.

In another aspect, the application provides a stable emulsion comprising one or more hydrophobic reactant(s) dissolved in a first solvent and emulsified droplets comprising ionic proteinaceous feedstock comprising an ionic fraction in a second solvent that is immiscible with said first solvent.

In another aspect, the application provides a stable emulsion comprising ionic proteinaceous feedstock comprising an ionic fraction dissolved in a first solvent and emulsified droplets comprising one or more hydrophobic reactant(s) in a second solvent that is immiscible with said first solvent.

In another aspect, the application provides a stable emulsion comprising one or more hydrophobic reactant(s) dissolved in a first solvent and emulsified droplets comprising ionic keratinaceous feedstock comprising an ionic fraction in a second solvent that is immiscible with said first solvent.

In another aspect, the application provides a stable emulsion comprising ionic keratinaceous feedstock comprising an ionic fraction dissolved in a first solvent and emulsified droplets comprising one or more hydrophobic reactant(s) in a second solvent that is immiscible with said first solvent.

DETAILED DESCRIPTION OF THE APPLICATION

The application involves functionalizing peptides, which include proteinaceous feedstocks including, but not necessarily limited to keratin, collagen, fibrin and other growth factors. A preferred proteinaceous feedstock is keratin derived from human hair or nails. A most preferred proteinaceous feedstock is keratin derived from hair which is harvested from the intended recipient of a medical implant or wound dressing to be used in treating said recipient. The keratin also may be derived from hair from a person other than the recipient. Other sources of keratin include but are not necessarily limited to animal hair, skin, hooves, horns, beaks, feet and feathers.

Keratins may be loosely defined as the hardened and insolubilized proteins found in the epidermal cells of vertebrates. Human hair is composed almost entirely of this proteinaceous, structural material. Keratins are afforded their structural integrity, in large part, by the presence of disulfide crosslinks which form a three dimensional network of polypeptide chains. This network structure renders keratins insoluble. Keratins can, however, be made water soluble by destroying this three dimensional structure via disulfide bond scission.

Disulfide bond scission can be performed either oxidatively, reductively, or using some combination of both types of bond scission. Oxidative bond scission with hydrogen peroxide, for example, results in the formation of sulfonic acid residues produced from cystine. The material produced using hydrogen peroxide is highly ionic and has excellent water solubility.

Reductive chemistries that are useful for disulfide bond scission in keratins in are described in Wardell, J. L., "Preparation of Thiols" in *The Chemistry of the Thiol Group*, Patai, S. (Editor), pp. 163–353, John Wiley & Sons, New York, N.Y. (1974), incorporated herein by reference. Reductive scission of cystine results in the formation of thiols. Thiols possess reactivities similar to alcohols, and can be used to perform a multitude of known organic chemical reactions, such as those described in McMurry, J., *Organic Chemistry*, Brooks/Cole Publishing Co., Monterey, Calif. (1984); Scudder, P. H., Electron Flow in Organic Chemistry, John Wiley & Sons, New York, N.Y. (1992); Stowell, J. C., *Intermediate Organic Chemistry*, John Wiley & Sons, New York, N.Y. (1994), incorporated herein by reference. These reactions can be used as the basis to tailor the properties of water soluble keratins.

The solubility characteristics of any solute molecule are dependent on the ability of solvent molecules to surround that solute molecule and interact in an energetically favorable manner. Solubility is achieved when the system energy is effectively lowered by solvent-solute interactions relative to solute-solute and solvent-solvent interactions. The ability of keratins to interact in an energetically favorable fashion with various solvent molecules can be manipulated by the way in which the keratin feedstock is chemically treated.

Proteins are normally hydrophilic due to the polar character of their amino acid backbone structure. In addition, pendent residues impart hydrophilic or hydrophobic character. For example, hydroxyl and carboxylic groups, such as those found in serine and glutamic acid, respectively, render proteins more hydrophilic, while hydrocarbon groups, such as those present in leucine, render proteins hydrophobic. This hydrophilic/hydrophobic character is intrinsic and dependent on the amino acid structure. Modification of amino acid residues can alter a protein's natural solubility characteristics. Particularly in the case of keratins, and due largely to the high percent cystine content, these proteins can be modified in ways that accentuate the influence of cysteine or modified cysteine on the entire molecule's solubility characteristics.

Amino acids generally have the formula:

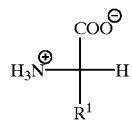

Table 1 summarizes the amino acid residues found in human hair, for example, and shows the "$R^1$" groups associated with each residue.

TABLE 1

Ranked average amounts of amino acids in human hair[1]

| Amino Acid | R¹ Group | Nature | pKa | Isoelectric Point (pH) | Percent Composition in Hair |
|---|---|---|---|---|---|
| Cysteine | H—S—CH$_2$— | Nonpolar | 8.4 | 5.02 | 17.3 |
| Glutamic Acid | HO—C(=O)—CH$_2$—CH$_2$— | Polar | 4.5 | 3.22 | 13.9 |
| Arginine | NH$_2$—C(=NH)—N(H)—(CH$_2$)$_3$— | Polar | 12.5 | 11.15 | 9.85 |
| Serine | HO—CH$_2$— | Polar | None | 5.68 | 9 |
| Threonine | CH$_3$—CH(OH)— | Polar | None | 5.64 | 7.75 |
| Leucine | (CH$_3$)$_2$CH—CH$_2$— | Hydrophobic | None | 5.98 | 7.35 |
| Proline | —CH$_2$—CH$_2$—CH$_2$— (ring) | Hydrophobic | None | 6.3 | 6.95 |
| Aspartic Acid | HO—C(=O)—CH$_2$— | Polar | 4.5 | 2.77 | 5.8 |
| Valine | (CH$_3$)$_2$CH— | Hydrophobic | None | 5.96 | 5.7 |
| Isoleucine | CH$_3$—CH$_2$—CH(CH$_3$)— | Hydrophobic | None | 5.94 | 4.75 |
| Glycine | H— | Nonpolar | None | 5.65 | 4.15 |
| Phenylalanine | C$_6$H$_5$—CH$_2$— | Hydrophobic | None | 5.48 | 3 |
| Alanine | CH$_3$— | Hydrophobic | None | 6 | 2.8 |
| Tyrosine | HO—C$_6$H$_4$—CH$_2$— | Hydrophobic | None | 5.66 | 2.6 |
| Lysine | NH$_2$—(CH$_2$)$_4$— | Polar | 10.4 | 9.59 | 2.5 |
| Histidine | imidazole—CH$_2$— | Aromatic | 6.2 | 7.47 | 0.9 |
| Methionine | CH$_3$—S—CH$_2$—CH$_2$— | Hydrophobic | None | 5.74 | 0.85 |

TABLE 1-continued

Ranked average amounts of amino acids in human hair[1]

| Amino Acid | R[1] Group | Nature | pKa | Isoelectric Point (pH) | Percent Composition in Hair |
|---|---|---|---|---|---|
| Tryptophan | 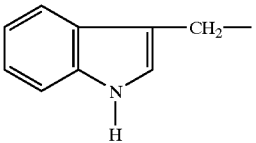 | Hydrophobic | None | 5.89 | 0.85 |

The most abundant amino acid in human hair is cysteine, which is found in the form of disulfide-bridged cystine groups.

The present application uses controlled treatment with one or both oxidizing and reducing reagents to balance the solubility properties of keratin peptides. As used herein, the phrase "soluble keratin peptides" are meant to include those keratin peptides that can be made soluble in water through treatment of the keratin source material using oxidative treatment, reductive treatment, or a combination of both. Soluble keratin peptides generally have a relatively low molecular weight, preferably about 15,000 or less, more preferably less than 12,000 daltons.

Oxidation/Reduction of Cystine Residues or "Primary Reactive Sites"

Solubility properties of water soluble keratin peptides may be "tuned" within certain limits by manipulating the ratio of ionic groups to polar groups in the keratin peptides. Ionic groups have a full positive or negative charge in water. Polar groups do not have an actual charge in water. Solubility properties of the keratin peptides also may be "tuned" by manipulating the type of ionic groups and polar groups in the peptides. The limit to which the solubility properties of the keratin peptide may be tuned is influenced by the relative amount of cystine present in the keratin feedstock, the effective conversion of cystine, and the relative amount and functionality of other amino acids.

Oxidation of keratin peptides with hydrogen peroxide or peracetic acid is used to convert cystine to sulfonic acid and peroxy acid residues, respectively. In general, the more of these acid residues present on a keratin peptide, the more soluble the resulting peptides will be in polar media, such as water.

In a preferred embodiment, the keratin source material (e.g. human hair), is oxidized by a suitable oxidizing agent. Suitable oxidizing agents include, but are not necessarily limited to hydrogen peroxide, peracetic acid, percarbonates, persulfates, chlorine dioxide, sodium and calcium peroxides, perborates, and hypochlorite. The oxidants are preferably used at a concentration up to about 35%, preferably at from about 0.1% to about 10%. The oxidation preferably occurs at reflux temperatures.

In a preferred embodiment, the hair is treated with hydrogen peroxide ($H_2O_2$), typically at concentrations up to about 35 percent, preferably from about 0.1% to about 10%, most preferably 1%, in order to disrupt the cuticle and swell the keratin source material. This process also converts some fraction of the cystine residues into sulfonic acid groups. The desired quantity of cystine residues converted to sulfonic acid groups depends upon the targeted solubility characteristics of the resultant soluble keratins. Where the desired characteristic is solubility in a relatively nonpolar medium, little to no oxidation is desired. Conversely, where the desired characteristic is solubility in a polar medium such as water, a large amount of oxidation is desired. The amount of oxidation is controlled by varying the time of oxidation, preferably from about 0 hours to about 4 hours, while retaining the other conditions of the oxidation reaction constant. These conditions include concentration and type of oxidant, temperature, and ratio of extracting media to keratin source material. After the reaction is complete, the oxidized hair is filtered and rinsed, preferably with deionized water. The filtrate is discarded and the hair is allowed to dry.

Where other conditions of oxidation are maintained constant, the conversion rate of cystine to sulfonic acid residues is roughly proportional to the amount of time used for the oxidation. The sulfonic acid groups impart ionic character to the resultant oxidized keratin solids and serve to improve the eventual solubility of subsequently reduced keratin peptides in polar media such as water.

Residual cystines in the resulting oxidized keratin solids are converted to other sulfur-containing moieties using reductive techniques. Preferably, the disulfide-bridged cystine group is converted to a thiol group, which has utility of it's own, or can be modified using a variety of chemical techniques. Suitable chemistries for modification of thiol groups include, but are not necessarily limited to formation of thioethers, nucleophilic addition reactions, including Michael addition reactions, condensation reactions, including but not necessarily limited to transesterification reactions.

Reaction with a Reducing Agent

A first method for reducing the cystine groups is reaction of the oxidized hair with a reducing agent. Suitable reducing agents include, but are not necessarily limited to ammonium thioglycolate, mercaptoethanol, dithiothreitol, thioglycerol, thiolactic acid, glutathione, cysteine, sodium sulfide, and sodium hydrosulfide. Preferred reducing agents are ammonium thioglycolate and mercaptoethanol, most preferably ammonium thioglycolate.

In order to treat the oxidized hair with the reducing agent, the previously oxidized hair is suspended in the reducing agent typically at a concentration of up to about 10N, preferably from about 0.1N and 1N; at a pH greater than about 7, preferably equal to or greater than 9, most preferably about 11; a temperature of from about 25 to about 80° C., preferably about 60° C., preferably for a time period of from about 1 to about 72, most preferably about 24 hours. The reaction occurs under an inert atmosphere, preferably nitrogen. The liquid fraction is separated from any remaining solids using known means, including but not necessarily limited to spray drying, or cannulation and/or centrifugation, preferably under inert atmosphere. A preferred method of separation is spray drying. Where cannulation/centrifugation is used, the soluble keratin peptides are isolated from the solution by addition of a non-solvent, or a solvent which is miscible with water, including but not necessarily limited to ethanol, methanol, isopropyl alcohol, tetrahydrofuran, acetone, dioxane, and the like, again under inert atmosphere. A preferred non-solvent is ethanol. The precipitate is separated from the non-solvent using known means, preferably by filtration and rinsing using additional aliquots of the non-solvent. The resulting keratin peptides are dried using known techniques, preferably overnight under vacuum at room temperature.

This process results in the further solubilization of the fraction of keratins having both sulfonic acid groups and thiol groups. The ratio of sulfonic acid to thiol is primarily controlled by the quantity of primary reactive sites remaining after oxidation. Of course, the rate of reduction will also be affected by reagent concentration(s), reaction temperature(s), and exposure time(s).

Control over the solubility characteristics of these soluble keratin peptides will be important in determining the full scope of potential chemical modifications that can be performed on the materials, as solubilization will be a necessary part of most subsequent reactions. For example, mutual solubilization of the keratins, reagents, and catalysts is the most preferred approach to chemical modification. However, in addition to mutual solubilization, it may be useful to use solid state chemistry, two phase chemistry, suspension or emulsion chemistry, and/or sol-gel chemistry.

In a preferred embodiment, the combined oxidation and reduction produces keratin peptides having an isoelectric band in the range of about 4.5.

Treatment of keratin peptides with reducing agents facilitates the formation of cysteine from cystine, but tends to leave the previously oxidized groups unaltered Although the cysteine residue is a polar residue, the cysteine residue has much less ionic character than an acid residue. As a result, treatment of keratin peptides with reducing agents produces a keratin peptide that has less ionic character, and—while somewhat soluble in polar solvents—is less soluble in water than peptides having solely ionic residues. Conversely, treatment of keratin peptides with reducing agents produces a keratin peptide that has more tendency to dissolve in organic solvent media that are less polar than water, including but not necessarily limited to alcohols, such as methanol, ethanol, and propanols; ethers and cyclic ethers such as tetrahydrofuran and 1,4-dioxane; ketones such as acetone; sulfones such as dimethylsulfoxide (DMSO); nitrogen-containing solvents such as amines and amides.

Compatibilization

Preferably, the target or desired solvent media solubilizes both the keratins and hydrophobic reactant(s), preferably "organic reactants," that are needed to further modify the keratins. The phrase "organic reactants," as used in the foregoing sentence, means compounds containing carbon. Suitable organic reactants include hydrocarbons and other organic materials, as well as materials having substantial water solubility, such as amines, esters, and ethers.

The present application provides systems effective to "compatibilize" (1) hydrophobic reactants and (2) proteinaceous materials comprising an ionic fraction by rendering these molecules thermodynamically compatible in a solution, suspension or emulsion. The resulting "stable solution," "stable suspension" or "stable emulsion" does not undergo gross phase separation into the respective pure components during processing. Preferred systems permit the formation of a sufficient quantity of covalent bonding between (1) and (2) to assist in preventing phase separation in the final product.

The chemically modified peptides, preferably keratins, are compatibilized with the relatively hydrophobic reactants, preferably organic reactant(s), using one of several techniques: 1) a mutual solvent that dissolves both the peptides and the hydrophobic reactants; 2) miscible solvents that solubilize the corresponding peptide or hydrophobic reactant, then are combined to form a stable solution; 3) immiscible solvents that form a stable suspension of a solution of either the peptide or the hydrophobic reactant in a solution of the other; or 4) a surfactant that forms a stable emulsion of neat or solution droplets of either the peptide or the hydrophobic reactant in a solution of the other. The compatibilization must be effective to produce intimate contact resulting in molecular collisions that cause reaction between functional groups on the hydrophilic peptides and hydrophobic reactant. Only certain systems are effective enough to compatibilize these types of materials.

The hydrophobic material would typically be nonpolar, and would be readily soluble in low surface tension fluids, including but not necessarily limited to low molecular weight hydrocarbons or alcohols, and most low molecular weight, nonpolar organic solvents, such as hexane, cyclohexane, benzene, and toluene, for example. Hydrophilic materials, on the other hand, are typically polar and would be readily soluble in higher surface tension fluids. Examples of higher surface tension fluids include, but are not necessarily limited to, liquid water, aqueous salt and protein solutions, dimethyl formamide, dimethyl sulfoxide, glycerol, hexamethyl phosphorictriamide, formamide, and glycols, for example.

The hydrophilic nature of proteinaceous materials is due to many factors, and can change based on the characteristics of the surrounding environment, namely pH. In some cases, these factors can be manipulated and the degree of hydrophilicity can be altered and controlled. In many proteinaceous systems, this is due primarily to the amphoteric character of proteins. One factor that is particularly useful as a means to manipulate the hydrophilicity of proteins is the electronic environment of the molecule itself. The electronic environment of a protein molecule can be manipulated simply by adjusting the pH of the solution.

Proteins are comprised of combinations of the 20 known amino acids. These amino acids can be broadly characterized as neutral, acidic, or basic. Neutral amino acids can be either polar or nonpolar. Acidic and basic amino acids can impart hydrophilicity, depending on pH, while neutral amino acids can impart hydrophilicity or hydrophobicity, depending on whether the pendant functional group (also know as the "R" group) is polar or nonpolar, respectively. The solubility of a given protein is determined by these amino acids, their relative amount, and the pH of their environment. For example, at low pH, basic groups such as amines can become protonated, resulting in a positive charge for that amino acid. At high pH, acidic groups such as carboxylic acids can become deprotonated, resulting in a negative charge for that amino acid. The sum of all of these positive and negative charges is the net charge. A protein with a net charge of zero is said to be at the isoelectric point. At the isoelectric point, proteins display "organic like" character. That is, they are nonionic on a macro scale, and therefore have the potential to adopt the solubility characteristics of organic, hydrophobic molecules. The degree to which a particular protein can be made hydrophobic depends on the proximity to their isoelectric point, and the influence of polarity of individual amino acids, even in the neutral state. For proteins who's functional groups can be changed through chemical manipulation, the isoelectric point can be altered through these chemical manipulations.

An excellent example of this is found in the chemistry of keratin proteins. Although the following explanation focuses on keratin, persons of ordinary skill in the art will understand that other molecules besides proteins have isoelectric points, that isoelectric points of these other types of molecules also may be manipulated, and that the specific technique described applies to other proteins as well as keratin. The manipulation of cysteine cleavage can have a dramatic effect on the solubility characteristics of keratins. Thus, by manipulating the relative amounts of cysteic acid and thiol, the isoelectric point, and thereby the solubility parameter, of a given keratin can be tuned. Tuning of the solubility parameter can be accomplished only to the extent allowed by the influence that the relative amount of cysteine provides in the presence of other polar amino acids. In the case of human hair, the influence of cysteine is significant. Table 1 ranks the average amount of various amino acids present in human hair. It is apparent from this table that cysteine is the most abundant amino acid contained in the keratins of human hair. However, Table 1 also suggests a large influence of acidic and basic groups such as those found in glutamic acid and arginine, respectively. There is also an appreciable amount of polar contribution from hydroxyl groups present on serine and threonine. To a lesser degree, hydrophobic character is imparted by the presence of numerous hydrocarbon-based amino acids. The net effect is a dominance by the acidic amino acids, as most forms of soluble keratins are acidic. Depending on the pH, however, the hydrophilic and hydrophobic character of solubilized keratins can be heavily influenced by the fate of the cysteine residues in human hair.

TABLE 1

Ranked average amounts of amino acids in human hair

| Amino Acid | R Group | Nature | pKa | Isoelectric Point (pH) | Percent Composition in Hair |
|---|---|---|---|---|---|
| Cysteine | H—S—$CH_2$— | Nonpolar | 8.4 | 5.02 | 17.3 |
| Glutamic Acid | HO—C(=O)—$CH_2$—$CH_2$— | Polar | 4.5 | 3.22 | 13.9 |
| Arginine | $NH_2$—C(=NH)—N(H)—$(CH_2)_3$— | Polar | 12.5 | 11.15 | 9.85 |
| Serine | HO—$CH_2$— | Polar | None | 5.68 | 9 |
| Threonine | $CH_3$—CH(OH)— | Polar | None | 5.64 | 7.75 |
| Leucine | $(CH_3)_2$CH—$CH_2$— | Hydrophobic | None | 5.98 | 7.35 |
| Proline | (cyclic $CH_2$—$CH_2$—$CH_2$—) | Hydrophobic | None | 6.3 | 6.95 |
| Aspartic Acid | HO—C(=O)—$CH_2$— | Polar | 4.5 | 2.77 | 5.8 |
| Valine | $(CH_3)_2$CH— | Hydrophobic | None | 5.96 | 5.7 |
| Isoleucine | $CH_3$—$CH_2$—CH($CH_3$)— | Hydrophobic | None | 5.94 | 4.75 |
| Glycine | H— | Nonpolar | None | 5.65 | 4.15 |

TABLE 1-continued

Ranked average amounts of amino acids in human hair

| Amino Acid | R Group | Nature | pKa | Isoelectric Point (pH) | Percent Composition in Hair |
|---|---|---|---|---|---|
| Phenylalanine | 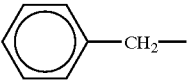 | Hydrophobic | None | 5.48 | 3 |
| Alanine | CH₃— | Hydrophobic | None | 6 | 2.8 |
| Tyrosine | 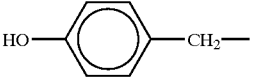 | Hydrophobic | None | 5.66 | 2.6 |
| Lysine | NH₂—(CH₂)₄— | Polar | 10.4 | 9.59 | 2.5 |
| Histidine | 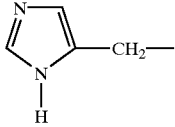 | Aromatic | 6.2 | 7.47 | 0.9 |
| Methionine | CH₃—S—CH₂—CH₂— | Hydrophobic | None | 5.74 | 0.85 |
| Tryptophan | 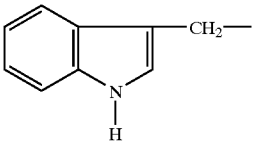 | Hydrophobic | None | 5.89 | 0.85 |

Through the use of oxidative and reductive chemistries, the isoelectric point of keratins (and other proteins) can be manipulated. It is through this tuning of the isoelectric point that systems for compatibilization can be optimized. By matching or nearly matching the solubility parameter of keratins with that of a hydrophobic reactant solution, compatibilized solutions of keratins and hydrophobic reactant can be prepared. While keratins, and most other proteins, cannot be made so organic at their isoelectric point that they become soluble in nonpolar solvents such as cyclohexane, sufficient organic character can be imparted to these molecules to make them mutually soluble with some select hydrophobic reactants. Once the hydrophilic protein is modified to be more hydrophobic, it can be reacted in solution with the hydrophobic reactant without the advent of "phase separation" during processing. Systems utilizing solutions, suspensions, and emulsions of keratins, in particular, can be utilized to produce substantially homogenous biomaterials. Keratins prepared at their isoelectric point have the potential to be solubilized in organic media that can also solubilize a hydrophobic reactant. In general, solvents with a "high dielectric constant" defined as 30 or greater, preferably greater than 30 have some ability to mutually solubilize both keratin at it's isoelectric point and a hydrophobic reactant.

Since crosslinking of the keratin would interfere with solubility, it is preferred that neither the ionic nor the hydrophobic reactants are effective as crosslinking agents. The modified proteins, preferably modified keratin peptides, comprise an "ionic fraction" and/or a "hydrophobic fraction." Although cystine-thioglycolate complexes may be present in the modified keratin peptides as a byproduct of preparation, the phrases "ionic fraction" and "polar fraction" refer to other than cystine-thioglycolate complexes.

Keratins prepared above or below their isoelectric point, by definition, possess a net charge. This makes them polar and hydrophilic. As such they would be most soluble in polar media such as water. To make a homogenous solution with a hydrophobic reactant, that reactant necessarily would be water soluble. However, homogenous solutions can be prepared by first preparing a solution of the hydrophobic reactant in a water-miscible organic solvent. Examples of water-miscible organic solvents include, but are not limited to alcohols such as methanol, ethanol, and propanols; ethers and cyclic ethers such as tetrahydrofuran and 1,4-dioxane; ketones such as acetone; sulfones such as dimethylsulfoxide; nitrogen-containing solvents such as amines and amides, etc. Once a stable, homogenous solution of the hydrophobic reactant in the water-miscible organic solvent is mixed with the high dielectric constant solution containing the keratin, the resulting dielectric constant of the new solution would necessarily need to be high enough to keep the keratin in solution, yet low enough to keep the hydrophobic reactant in solution.

A useful system comprises a suspension of a miscible solvent in an immiscible solvent. For example, to a solution of keratin in water is added a solution of hydrophobic reactant in a nonpolar solvent. Typically, solvents with a dielectric constant of 10 or less, preferably less than 10 are immiscible in water and could be used. Using mechanical agitation, a suspension of one solution in the other is created and the keratin reacts with the hydrophobic reactant at the interface between the suspended droplets and the matrix solution. The mechanical agitation and droplet formation increases the surface area at which the materials can react.

Another suitable immiscible solvent system is one in which a surfactant is used to form a stable emulsion. Surfactants function by stabilizing the interface between the droplets or micelles, and the surrounding solvent matrix. Surfactant materials typically contain both a hydrophilic and a hydrophobic structure in the same molecule. This allows the surfactant to position itself between the hydrophilic and hydrophobic materials at the micelle interface. The surfactant can also act as a phase transfer catalyst, facilitating the reaction between the keratin molecules in one phase and the hydrophobic reactant in the other phase.

These four systems, 1) mutual solvation; 2) miscible cosolvents; 3) suspension using immiscible solvents; and 4) emulsion using immiscible solvents and a surfactant, form the basis of the solvent systems for compatibilizing hydrophobic reactants and relatively hydrophilic proteinaceous feedstock for copolymerization. So long as the copolymerization chemistry is compatible with these approaches, these four systems can be used to form the desired copolymers.

The following are examples of reactions that may be used to chemically modify the proteinaceous feedstoc, preferably a keratinaceous feedstock. A number of the reactions described below occur in an anhydrous solvent. Persons of ordinary skill in the art will recognize that anhydrous solvents include a large number of solvents, including, but not necessarily limited to 1,2,-dimethoxyethane, dimethylformamide, DMSO, N-methylpyrrolidone, and others.

Production of Thioester

A preferred reductive modification is the formation of a thiolate anion, followed by nucleophilic substitution employing an appropriate leaving group, yielding a thioether. An example of this reaction scenario is shown in Scheme 1.

Scheme 1.
$S_N 2$ Reaction of cysteine in the thiolate anion form with RX, preferably an alkylhalide

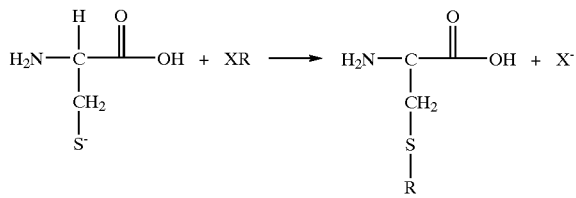

The "R" group in Scheme 1 is selected from the group consisting of elements that bond with sulfur, preferably elements that covalently bond with sulfur. Such elements include, but are not necessarily limited to alkyls, aryls, silanes, silicones. Preferred elements are selected from the group consisting of alkyl and aryl halides. The particular "R" group selected depends upon the desired properties of the resultant modified keratin. The thiolate anion can be generated from thiol, or more directly from the keratin feedstock, by reaction with a reactive nucleophile. Suitable nucleophiles include alkyl and aryl sulfide salts, sulfonates, cyanates, thiocyanates, halides, hydrosulfide, hydroxide, alkoxides, azides, and acetates preferably alkyl and aryl sulfide salts, hydrosulfide, hydroxide, alkoxides, azides, and acetates. A preferred reactive sulfur-containing compound is sodium sulfide.

The "X" group in Scheme 1 is a group adapted to be displaced from the R group by a sulfur anion. Suitable X groups are selected from the group consisting of halides, tosylates, acetates, hydroxyls, alkoxys, and amines, preferably halides, tosylates and acetates. Most preferred X groups are halides.

In order to perform this reaction, the keratin source material is first oxidized in solution. The liquid fraction is removed and discarded, and the solid keratin rinsed of residual oxidant and then reduced, using, for example, an aqueous solution of sodium sulfide. The aqueous phase is separated from any remaining keratin solid, and the solubilized keratins are isolated from solution as thiolate salts. Residual reductant and side reaction products can be removed from the keratin salts by a variety of procedures such as extraction, for example. The purified keratin is then exposed to a solution of "RX", preferably an alkyl halide, in toluene and a catalytic amount of phase transfer catalyst is added to expedite the reaction. The RX is typically at a concentration of up to about 20 mole percent relative to keratin, preferably from about 5 to 10 mole percent relative to keratin; at a pH greater than about 7, preferably greater than 9; a temperature of from about 20 to about 100° C., preferably about 60° C., preferably for a time period of from about 1 to about 72 hours, most preferably about 24 hours. Preferred alkyl halides are selected from the group consisting of alkyl iodides, alkyl bromides, and alkyl chlorides, preferably alkyl iodides and alkyl bromides, most preferably alkyl iodides.

Conversion of Thiol by Addition

An addition reaction, such as a Michael addition to an unsaturated hydrocarbon, represents another potential avenue to transformation of the thiol group. Michael, J., *J. Prakt. Chem.*, 35(2), p. 349 (1887), incorporated herein by reference. The Michael addition reaction consists of addition of a nucleophile to an activated alkene. An activated alkene is an alkene which is conjugated with an electron withdrawing group such as a carbonyl group, a nitrile group, a nitro group, an allyl group, and others. The Michael reaction is exemplified in Scheme 2.

Scheme 2.
The Michael addition reaction

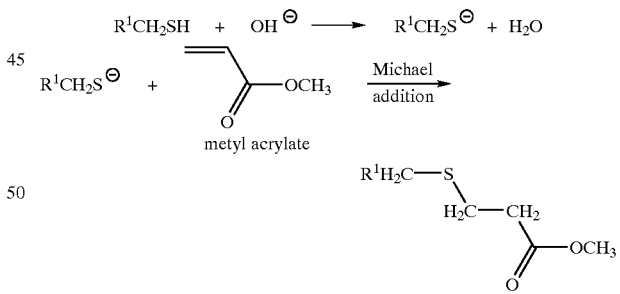

In Scheme 2, $R^1CH_2SH$ is a cysteine residue in a keratin peptide and the methyl acrylate is a Michael acceptor. In order to perform this reaction, the keratin source material is first oxidized in solution. The liquid fraction is removed and discarded, and the solid keratin rinsed of residual oxidant and then reduced, using, for example, an aqueous solution of thioglycolate. The aqueous phase is separated from any remaining keratin solid, and the solubilized keratins are isolated from solution as thiols. Residual reductant and side reaction products can be removed from the keratins by a variety of procedures such as by extraction, for example. The purified keratins are exposed to a solution of sodium hydroxide, sufficient to convert the thiol residue to its sulfide anion. In the Michael addition, a Michael acceptor, such as methyl acrylate, is added to the keratin solution, typically at a concentration of up to about 20 mole percent relative to the keratins, preferably 5 to 10 mole percent relative to the keratins; at a pH about 7, preferably between 6 and 8; a temperature of from about 20 to about 100° C., preferably about 60° C., preferably for a time period of from about 1 to about 72, most preferably about 24 hours.

A second way to convert a thiol to a less ionic moiety is to add the thiol across a carbon-carbon double bond of a "normal" alkene in the presence of a free radical precursor, preferably dissolved in an anhydrous solvent, to the aqueous solution of the purified keratin. Scheme 2' illustrates this reaction:

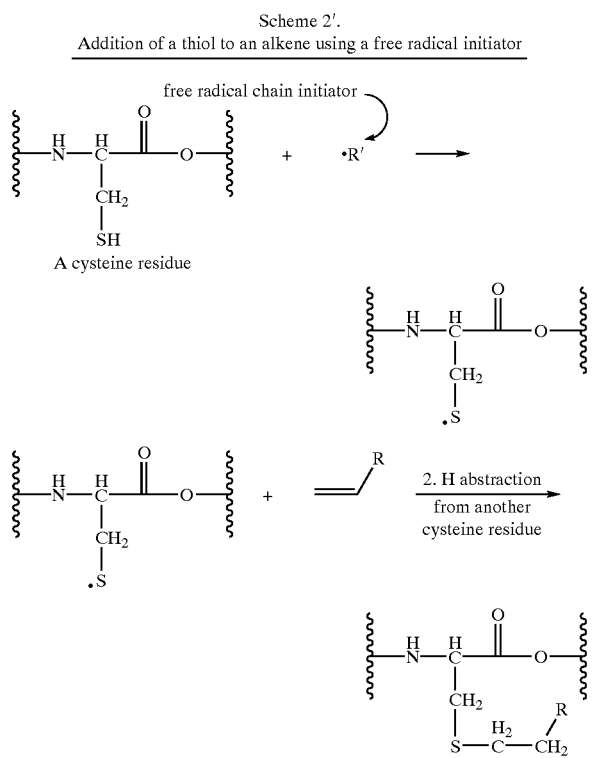

In Scheme 2', R is selected from the group consisting of silanes, silicones, and alkyl groups having from about 1 to about 6 carbon atoms.

In order to perform this reaction, the keratin source material is first oxidized in solution. The liquid fraction is removed and discarded, and the solid keratin rinsed of residual oxidant and then reduced, using, for example, an aqueous solution of thioglycolate. The aqueous phase is separated from any remaining keratin solid, and the solubilized keratins are isolated from solution as thiols. Residual reductant and side reaction products can be removed from the keratins by a variety of procedures such as extraction, for example. The purified keratins are exposed to a solution of the alkene in anhydrous solvent, typically at a concentration of up to about 20 mole percent relative to the keratins, preferably 5 to 10 mole percent relative to the keratins; at a pH about 7, preferably between 6 and 8; a temperature of from about 20 to about 100° C., preferably about 60° C., preferably for a time period of from about 1 to about 72, most preferably about 24 hours. Sufficient anhydrous solvent is added to the reaction to keep the alkene in solution with the keratin. Free radical precursors are typically initiated by heat or irradiation. Free radical photoinitiators include, but are not limited to benzoin ethers, benzil ketals, α-dialkoxyacetophenones, α-hydroxyalkylphenones, α-aminoalkylphenones, acylphosphine oxides, benzophenone/amines, thioxanthones/amines, titanoocenes, and certain silanes.

Another thiol addition involves nucleophilic addition. In order to perform nucleophilic addition, the keratin is first oxidized in solution. The liquid fraction is removed and discarded, and the solid keratin rinsed of residual oxidant and then reduced, using, for example, an aqueous solution of thioglycolate. The aqueous phase is separated from any remaining keratin solid, and the solubilized keratins are isolated from solution as thiols. Residual reductant and side reaction products can be removed from the keratins by a variety of procedures such as extraction, for example. The purified keratins are exposed to a solution of the allyl derivative, preferably those allyl derivatives that are soluble in the same solvent media as the keratins, typically at a concentration of up to about 20 mole percent relative to the keratins, preferably 5 to 10 mole percent relative to the keratins; at a pH of about 7, preferably between 6 and 8; a temperature of from about 20 to about 100° C., preferably about 60° C., preferably for a time period of from about 1 to about 72 hours, most preferably about 24 hours. The reaction may be promoted by a suitable catalyst, such as alumina, or a free radical initiator typically initiated by heat or irradiation. Free radical photoinitiators include, but are not limited to benzoin ethers, benzil ketals, α-dialkoxyacetophenones, α-hydroxyalkylphenones, α-aminoalkylphenones, acylphosphine oxides, benzophenone/amines, thioxanthones/amines, titanoocenes, and certain silanes.

Conversion of Thiol by Condensation

Condensation reactions such as transesterification, for example, can be used to generate thioesters. An example of a transesterification reaction is shown in Scheme 3.

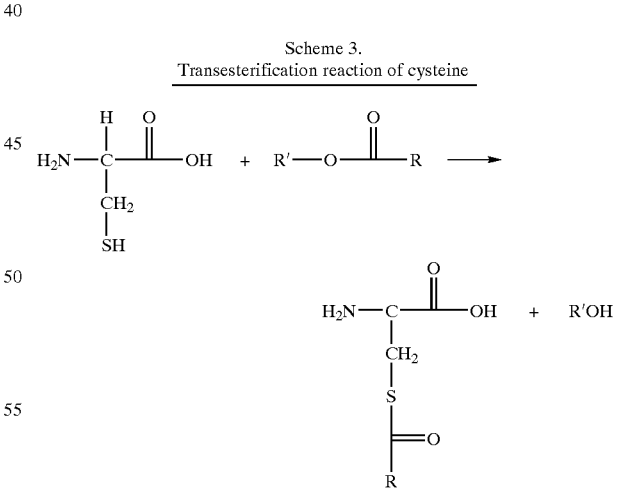

In order to perform this reaction, the keratin source material is first oxidized in solution. The liquid fraction is removed and discarded, and the solid keratin rinsed of residual oxidant and then reduced, using, for example, an aqueous solution of thioglycolate. The aqueous phase is separated from any remaining keratin solid, and the solubilized keratins are isolated from solution as thiols. Residual reductant and side reaction products are removed from the keratins by a variety of procedures such as extraction, for example. The purified keratins are exposed to a solution of the ester, preferably esters having from about 1 to 3 carbon atoms (methyl, ethyl, and propyl esters, respectively) of desired alkyl and aryl carboxylic acids, typically at a concentration of up to about 20 mole percent relative to keratin, preferably between 5 and 10 mole percent relative to keratin; at a pH less than about 7, preferably less than 5; a temperature of from about 0 to about 100° C., preferably about 60° C., preferably for a time period of from about 1 to about 72, most preferably about 24 hours. Mineral acid catalysts, such a hydrochloric acid, can typically be employed.

Other reaction scenarios, such as those directed toward polymer synthesis, also are useful to convert thiols to an assortment of desirable functional residues, including those described in Rempp, P. and Merrill, E. W., *Polymer Synthesis*, Huethig & Wepf Verlag Basel, Heidelberg, Germany (1986); Young, R. J. and Lovell, P. A., *Introduction to Polymers*, Chapman & Hall, London (1991); Odian, G., *Principles of Polymerization*, John Wiley & Sons, New York, N.Y. (1991), incorporated herein by reference.

Functionalization of "Secondary Reactive Sites"

As reflected in Table 1, in addition to cystine, keratins contain numerous secondary functional groups or "secondary reactive sites" within their amino acid sequences. Many of these secondary reactive sites are chemically labile, and some are found in relative abundance that is nearly equal to that of cysteine groups. The most important of these secondary reactive sites are: (a) carboxylic acid groups, present in glutamic and aspartic acid; (b) amine groups, present in arginine; and, (c) hydroxyl groups, present in serine and threonine. These secondary reactive sites, (a)–(c), collectively comprise 46.3 percent of the potential reactivity of keratins. Cysteine, by comparison, has a relative abundance of 17.3 percent in human hair.

The present application provides for even finer "tuning" of the solubility characteristics of a given keratin peptide by chemically modifying these secondary reactive sites.

The reactivities of carboxylic acids, amines, and alcohols are well known in organic and polymer chemistry. Examples of the types of reactions that each group can undergo are shown in Table 2.

TABLE 2

Reactions of secondary functional groups found in keratins

| Functional Group | General Reactions |
|---|---|
| Carboxylic Acid | deprotonation (generation of a nucleophile), decarboxylation, reduction, alpha substitution, nucleophilic acyl substitution |
| Amine | alkylation, acylation, elimination, addition |
| Hydroxyl | dehydration, deprotonation, oxidation, condensation, esterification, alkylation (ether synthesis) |

Reactions of Carboxylic Acids

In each of the following paragraphs describing reactions of carboxylic groups, "$R^1$—COOH" represents an $R^1$ group of a keratin peptide comprising a carboxylic acid residue, such as glutamic acid or aspartic acid.

Deprotonation of COOH

A preferred embodiment of deprotonation of a carboxylic group (generation of a nucleophile) is illustrated below:

Scheme 4.
Deprotonation of carboxylic acid

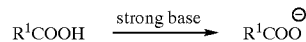

Deprotonation of a carboxylic group is useful to render the resulting residue reactive toward Lewis acids.

In order to perform this reaction, solubilized keratins are exposed to a solution of the base, preferably NaOH, preferably in a polar organic solvent such as an alcohol, typically at a concentration of up to about 20 mole percent relative to keratin, preferably between 5 and 10 mole percent relative to keratin; at a pH greater than about 7, preferably greater than 9; a temperature of from about 0 to about 100° C., preferably about 60° C., preferably for a time period of from about 0 to about 72, most preferably about 24 hours.

Decarboxylation

A preferred embodiment of decarboxylation is illustrated below:

Scheme 5.
Decarboxylation of a carboxylic acid over a catalyst

Suitable catalysts include nickel and copper, preferably copper. Decarboxylation is useful to render the resulting residue essentially nonfunctional. Conceivably, reactions of this type are effective at removing polar carboxylic acid functionality and transforming these groups to hydrophobic hydrocarbon groups.

In order to perform this reaction, solubilized keratins are exposed to a solution containing a metal catalyst, typically copper, typically at a concentration of up to about 20 mole percent relative to keratin, preferably between 5 and 10 mole percent relative to keratin; at a temperature of from about 0 to about 200° C., preferably about 100° C., for a time period sufficient to complete the reaction, suitably from about 0 to about 72 hours, preferably about 24 hours.

Reduction of COOH

A preferred embodiment of reduction of a carboxylic group is depicted below:

Reduction of a carboxylic group is useful to render the resulting residue less acidic than the corresponding carboxylic acid, thereby reducing the ionic character of the residue.

In order to perform this reaction, keratin peptides which are solubilized in anhydrous solvent, are exposed to an anhydrous solution containing a reducing agent, including but not necessarily limited to hydride reagents including but not necessarily limited to lithium aluminum hydride, typically at a concentration of up to about 20 mole percent relative to the keratin peptides, preferably from about 5 to about 10 mole percent relative to the keratin peptides; at a temperature of from about 0 to about 200° C., preferably about 100° C., preferably for a time period of from about 0 to about 72 hours, most preferably about 24 hours. Further exposure of reaction products to aqueous acid results in the formation of the corresponding alcohol.

Alpha Substitution of COOH

A preferred embodiment of alpha substitution of a carboxylic group is shown below:

Scheme 7.
Alpha halogenation of a carboxylic acid

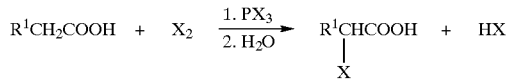

wherein X is selected from the group of halogen atoms, including but not necessarily limited to fluorine, chlorine, bromine, and iodine, preferably bromine, and is catalyzed by the corresponding phosphorous trihalide, preferably phosphorous tribromide. Alpha substitution of a carboxylic group is useful to render the resulting residue multifunctional in that this process conserves the carboxylic functionality while adding the halogen.

In order to perform alpha bromination, solubilized keratins are exposed to a solution containing bromine in a suitable anhydrous solvent, typically at a concentration of up to about 20 mole percent relative to keratin dissolved in the anhydrous solvent, preferably between 5 and 10 mole percent relative to keratin in the anhydrous solvent; in the presence of phosphorus tribromide catalyst and at a temperature of from about 0 to about 100° C., preferably about 30° C., preferably for a time period of from about 0 to about 72 hours, most preferably about 24 hours. Further exposure of reaction products to water results in the formation of the corresponding α-bromo carboxylic acid.

Nucleophilic Acyl Substitution of COOH

Nucleophilic acyl substitution of a carboxylic group is illustrated below:

Scheme 8.
Nucleophilic acyl substitution

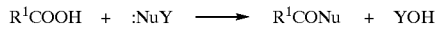

wherein the nucleophile (:NuX) is selected from the group comprising esters, amines, alcohols, and chlorinating reagents such as thionyl chloride, where X is the non-nucleophilic group of the molecule and is a hydrogen when NuX is an alcohol or an amine. Nucleophilic acyl substitution of a carboxylic group is useful to render the resulting residue less ionic in nature and potentially more hydrophobic, depending on the alkyl group associated with the nucleophile.

In order to perform this reaction, the acyl oxygen of the carboxylic acid is typically protonated using a mineral acid (acid catalyzed). This renders the ionic character of the acyl carbon more positive, thus making the acyl carbon a better site for nucleophilic attack. This can be accomplished by exposing solubilized keratins to a solution containing the nucleophilic compound, typically at a concentration of up to about 20 mole percent relative to keratin, preferably between 5 and 10 mole percent relative to keratin; at a pH less than 7, preferably less than 5; at a temperature of from about 0 to about 100° C., preferably about 60° C., preferably for a time period of from about 0 to about 72 hours, most preferably about 24 hours.

Modification of Amine Groups

In each of the following, $R^1$—$NH_2$ represents an $R^1$ group of a keratin peptide comprising an amine group, such as arginine.

Alkylation of Amine Groups

A preferred embodiment of alkylation of an amine group is depicted below:

Alkylation of an amine group is useful to transform a primary amine into a secondary amine, thereby altering the resulting reactivity of the residue. Additionally, two equivalents of the alkylation reagent can be added to fully convert the amine to a tertiary amine.

Secondary alkyl amines are generally more basic than the corresponding primary amines, presumably because alkyl groups are electron donating, making the free electron pair on the nitrogen more available. Almost all of the primary alkyl amines have $pK_a$'s ranging from 10.4 to 10.65; whereas, most secondary amines range in $pK_a$ from 10.7 to 11.2 $PK_a$'s of many tertiary alkyl amines fall within 9.8 to 10.7. The reason for this range and its average magnitude are not easily explained. However, the free electron pair on tertiary amines, because of more stearic hinderance, are, on average, less available for protonation than primary and secondary amines. This effect, then, slightly overcomes the increased electron electron donation by the 3 alkyl groups.

In order to alkylate amine groups, solubilized keratins are exposed to a solution containing an alkylating reagent dissolved in a suitable anhydrous solvent, including but not limited to alkyl halides containing 1 to 5 carbon atoms, typically at a concentration of up to about 20 mole percent relative to keratin, preferably between 5 and 10 mole percent relative to keratin; at a pH greater than 7, preferably greater than 9; at a temperature of from about 0 to about 100° C., preferably about 60° C., preferably for a time period of from about 0 to about 72 hours, most preferably about 24 hours. During the reaction, sufficient anhydrous solvent is added to keep the alkylating agent in solution with the keratin.

Acylation of Amino Groups

A preferred embodiment of acylation of an amino group is depicted below:

Scheme 9.
Acylation of an amino group

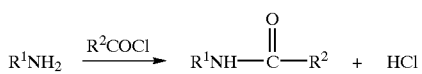

wherein $R^2$ is selected from the group consisting of alkyl groups containing from about 1 to 5 carbon atoms, and aromatic groups. Acylation of an amino group is useful to transform a primary amine into a secondary amide, thereby altering the resulting reactivity of the residue. Additionally, two equivalents of the acylating reagent can be added to fully convert the amino group to an amido amide. Substitution of hydrogen atoms with acyl functionality reduces the residue's ionic character.

Elimination of Amine Groups

A preferred embodiment of elimination of an amine group is illustrated below:

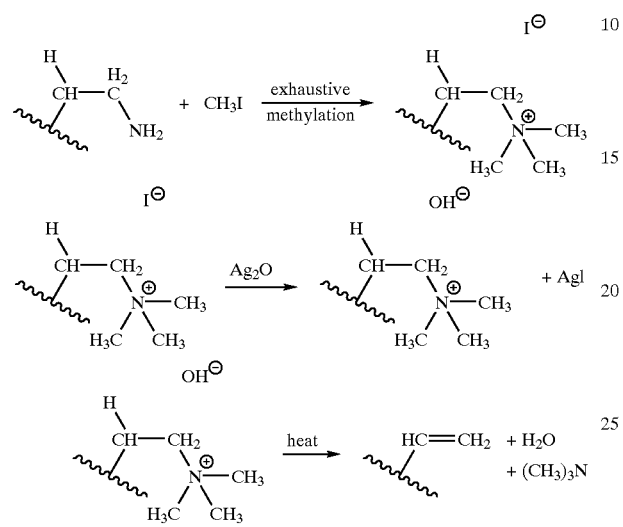

In order to accomplish this reaction, the free —NH$_2$ groups are exhaustively methylated using known means, such as by dissolving the keratin in a 50/50 solution of anhydrous solvent/water, such as 50/50=DMF/water, then adding excess methyl iodide and refluxing for 2 hours. The unreacted Me-I is stripped, and a stoichiometric amount of AgO (silver oxide) is added to the exhaustively methylated keratin to convert the iodide anion to hydroxide. The insoluble AgI is filtered, and the filtrate is heated to from about 120 to about 150° C. for 3 hours. Elimination of the amine and transformation to the corresponding alkene renders the residue more hydrophobic.

Addition of Amine Groups

A preferred embodiment of addition of amine or amino groups is shown

Scheme 11.
Reaction of amino groups with oxiranes (epoxides)

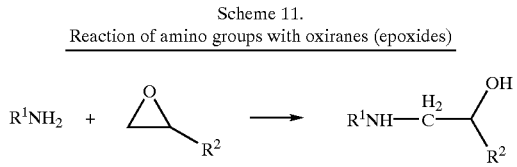

below:

wherein R$^2$ is selected from the group consisting of a phenyl group, a hydrogen or alkyl group ranging from 1 to 6 carbon atoms. Addition reactions between amines and oxirane compounds occur readily without the aid of a catalyst. Addition using an amine group is useful to transform a primary amine into a secondary amine, thereby altering the resulting reactivity and ionic character of the residue. Additionally, two equivalents of the addition reagent can be added to fully convert the amine to a tertiary amine. Substitution of hydrogen atoms with alkyl functionality reduces the residue's ionic character.

In order to perform this reaction, solubilized keratins are exposed to a solution containing an oxirane-containing aliphatic or aromatic compound, typically at a concentration of up to about 20 mole percent relative to keratin, preferably between 5 and 10 mole percent relative to keratin; at a pH greater than 7, preferably greater than 9, or less than 7, preferably less than 6; at a temperature of from about 0 to about 100° C., preferably about 30° C., preferably for a time period of from about 0 to about 72 hours, most preferably about 24 hours.

Modification of Hydroxyl Groups

In each of the following,

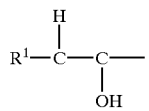

R$^1$—OH, or R$_1$—CH$_2$OH, represents an R$^1$ group of a keratin peptide comprising a hydroxyl group, such as serine and threonine.

A preferred embodiment of dehydration of a hydroxyl group is described below:

Scheme 12.
Dehydration of alcohols

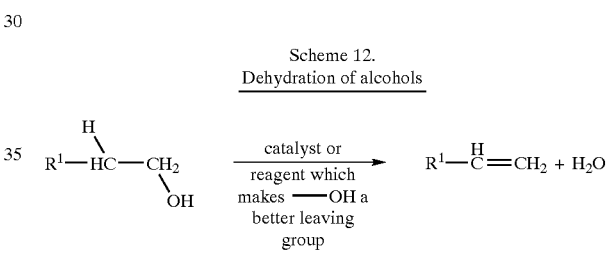

Dehydration of an alcohol group produces an alkene which is less polar than the alcohol.

In order to perform this reaction, solubilized keratins, dissolved in a suitable anhydrous solvent are exposed to a solution containing a dehydration catalyst or activating reagent also dissolved in anhydrous solvent, including but not limited to stoichiometric phosphorus oxychloride, typically at a concentration of up to about 20 mole percent relative to keratin, preferably between 5 and 10 mole percent relative to keratin; at a pH greater than 7, preferably between 7 and 10; at a temperature of from about 0 to about 100° C., preferably about 0° C., preferably for a time period of from about 0 to about 72 hours, most preferably about 24 hours.

Deprotonation of Hydroxyl Groups

A preferred embodiment of deprotonation of a hydroxyl group is illustrated below:

Scheme 13.
Conversion of alcohols to their oxyanion

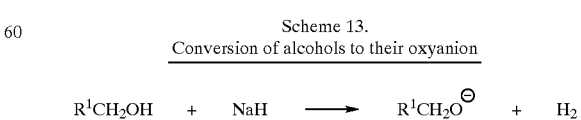

Deprotonation of a hydroxyl group is useful to render the residue reactive toward Lewis acids.

In order to perform this reaction, solubilized keratins, dissolved in an aprotic solvent, such as 1,2-dimethoxyethane, are exposed to a solution containing a strong base, including but not limited to sodium hydride, also dissolved in a suitable anhydrous solvent at a temperature of from about 0 to about 100° C., preferably about 30° C., preferably for a time period of from about 0 to about 3 hours, most preferably about 30 minutes.

Oxidation of Hydroxyl Groups

A preferred embodiment of oxidation of a hydroxyl group is given below:

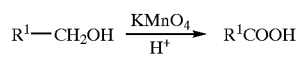

Oxidation of a hydroxyl group is useful to impart greater ionic character to the keratin peptides through the carboxylic acid functionality In order to perform this reaction, solubilized keratin peptides in a suitable anhydrous solvent are exposed to a solution of an oxidizing reagent, preferably potassium permanganate, at a concentration of up to about 20 mole percent relative to the keratin peptides, preferably between 5 and 10 mole percent relative to keratin; at a pH less than about 7, preferably less than 5; a temperature of from about 0 to about 30° C., preferably about 0° C., preferably for a time period of from about 0 to about 24 hours, most preferably about 8 hours.

Condensation of Hydroxyl Groups

A preferred embodiment of condensation of a hydroxyl group is given below:

Scheme 14.
Condensation of alcohols to form ethers

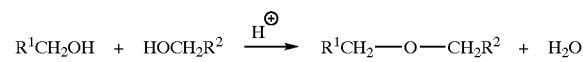

Condensation of a hydroxyl group is useful to render the residue less polar through the formation of the resulting alkyl ether, for example.

In order to perform this reaction, solubilized keratins are exposed to a solution containing an alcohol, including but not limited to aliphatic alcohols comprising from about 1 to 5 carbons, in the presence of strong mineral acid; at a temperature of from about 0 to about 100° C., preferably about 60° C., preferably for a time period of from about 0 to about 72 hours, most preferably about 24 hours.

Esterification of Hydroxyl Groups

A preferred embodiment of esterification of a hydroxyl group is illustrated below:

Scheme 15.
Esterification of alcohols to form esters

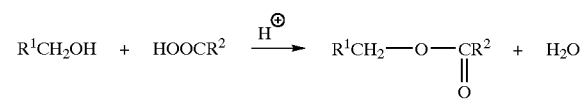

Esterification of a hydroxyl group is useful to impart greater ionic character to the keratin peptides than that imparted by the corresponding alcohol.

In order to perform this reaction, keratin peptides, solubilized in an anhydrous solvent, are exposed to a solution of the ester, preferably 1 to 3 carbon esters (methyl, ethyl, and propyl esters, respectively) of desired alkyl and aryl carboxylic acids, typically at a concentration of up to about 20 mole percent relative to keratin, preferably between 5 and 10 mole percent relative to keratin; at a pH less than about 7, preferably less than 5; a temperature of from about 0 to about 100° C., preferably about 60° C., preferably for a time period of from about 1 to about 72 hours, most preferably about 24 hours.

Alkylation of Hydroxyl Groups

A preferred embodiment of alkylation (ether synthesis) of a hydroxyl group, is illustrated below:

Scheme 16.
Alkylation of alcohols

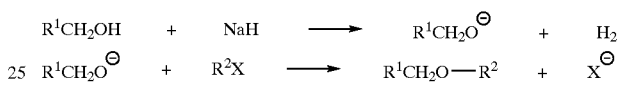

Alkylation of a hydroxyl group is useful to render the residue less polar than the corresponding alcohol.

In order to perform this reaction, the solubilized keratin is treated with strong base in an aprotic solvent, such as 1,2-dimethoxyethane. The keratin peptides bearing deprotonated hydroxyl groups are exposed to a solution containing an alkylating reagent, including but not limited to alkyl halides containing 1 to 5 carbon atoms, typically at a concentration of up to about 20 mole percent relative to the keratin peptides, preferably between 5 and 10 mole percent relative to keratin; at a temperature of from about 0 to about 100° C., preferably about 60° C., preferably for a time period of from about 0 to about 72 hours, most preferably about 24 hours.

Addition of Isocyanate to Hydroxyl Groups

The addition of isocyanate to a hydroxyl group is shown below:

Scheme 17
Addition of an alcohol group to an isocyanate

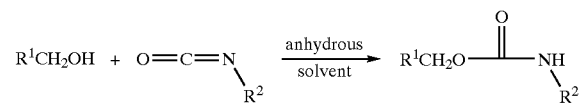

The addition of isocyanate to hydroxyl residues is useful to render the residue less polar than the corresponding hydroxyl residue, presuming that the isocyanate is highly aliphatic.

In order to perform this reaction, keratin peptides dissolved in a suitable anhydrous solvent are exposed to a solution containing the isocyanate-containing reagent in an aprotic solvent, such as DMF, including but not limited to alkyl, aryl, benzyl, and allyl isocyanates containing 1 to 8 carbon atoms, typically at a concentration of up to about 20 mole percent relative to keratin dissolved in the same aprotic solvent, preferably between 5 and 10 mole percent relative to keratin; at a temperature of from about 0 to about 100° C., preferably about 60° C., preferably for a time period of from about 0 to about 72 hours, most preferably about 24 hours. Reaction efficiencies can be enhanced with the use of metal catalysts including, but not limited to organotin compounds, preferably dibutyltin dilaurate.

Use of Multiple Reagents and/or Catalysts

The use of multiple reagents and/or catalysts permits the conversion of these secondary reactive sites using many more specific and elegant reactions. For example, esterification of a carboxylic acid group is accomplished by reaction with an alcohol or glycol in the presence of a catalyst, as shown below:

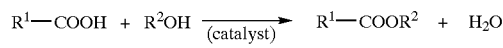

where R$^1$—COOH is an amino acid group, such as glutamic or aspartic acid, and R$^2$ is selected from the group consisting of alkylene groups having from about 1 to about 12 carbon atoms. Potential catalysts include acetates of sodium, manganese, zinc, calcium, cobalt, or magnesium, antimony (III) oxide, and titanium alkoxides.

Using the foregoing esterification scheme, the residue may be substituted with R$^2$ groups having particular desired polarity, charge, etc.

In order to perform this reaction, solubilized keratins are exposed to a solution containing an aliphatic alcohol reagent, including but not limited to alkyl alcohols containing 1 to 5 carbon atoms, typically at a concentration of up to about 20 mole percent relative to keratin, preferably between 5 and 10 mole percent relative to keratin; at a pH between 5 and 9, preferably between 6 and 8; at a temperature of from about 0 to about 100° C., preferably about 60° C., preferably for a time period of from about 0 to about 72 hours, most preferably about 24 hours. If titanium alkoxides are used, water must be replaced with an anhydrous solvent, such as DMF. A similar reaction with anhydrides can also be performed with the same types of catalysts to achieve similar results.

The application provides modified proteins, preferably modified keratin peptides, that are soluble in various solvents. Suitable modified keratin peptides generally have a molecular weight of about 15,000 or less, preferably about 12,000 or less, and comprise an ionic fraction of amino acid residues comprising oxidized reactive sites and a polar fraction of amino acid residues comprising chemically modified functionalities selected from the group consisting of unoxidized primary reactive sites and secondary reactive sites. The polar fraction is at a ratio to said ionic fraction effective to provide for solubility in a desired solvent. In a preferred embodiment, the modified keratin peptides have an isoelectric band that is compatible with the desired solvent. A preferred embodiment is modified keratin peptides having an isoelectric band of about 4.5.

In a preferred embodiment, the chemically modified functionalites on the modified keratin peptides are selected from the group consisting of: thioethers; products of nucleophilic addition to thiols; products of condensation with thiols. In other embodiments, the chemically modified functionalities are further selected from the group consisting of modified carboxylic acid residues, modified amine residues, and modified hydroxyl residues. In other aspects, said chemically modified carboxylic acid residues are selected from the group consisting of deprotonated carboxylic acid residues; decarboxylated carboxylic acid residues; reduced carboxylic acid residues; alpha substituted carboxylic acid residues; and nucleophilic acyl substituted carboxylic acid residues. In another aspect, said chemically modified amine residues are selected from the group consisting of alkylated amines, acylated amines, the product of eliminating amines, and the product of addition to amines. In another aspect, said chemically modified hydroxyl residues are selected from the group consisting of dehydrated hydroxyl groups, deprotonated hydroxyl groups, oxidized hydroxyl groups, the product of condensation with hydroxyl groups, esterified hydroxyl groups, and alkylated hydroxyl groups.

The application will be better understood with reference to the following Examples, which are illustrative only:

EXAMPLE 1

Oxidation of Human Hair 500 g of clean, dry hair was placed in a 12-liter glass reactor with a TEFLON™-coated magnetic stir bar. 8380 mL of a 1 weight/volume percent solution of hydrogen peroxide (H$_2$O$_2$) was added and the hair was completely wetted and immersed. The reactor was fitted with a lid and water-cooled condenser, and the reaction heated to reflux for varying time periods from 0 to 180 minutes, specifically for 0, 30, 60, 120, and 180 minutes, with stirring. After the time period was complete, the reactor was disassembled and the hair immediately filtered and rinsed with deionized (DI) water. The filtrate was discarded and the oxidized hair allowed to air dry.

The samples were each separately reduced in subsequent steps.

Reduction of Oxidized Human Hair

The pH of a 1N thioglycolate solution was adjusted to 11 using ammonium hydroxide. 10 g of air-dried, oxidized hair was placed in a 250 mL glass reaction flask with a TEFLON™-coated magnetic stir bar. 100 mL of the 1N solution of thioglycolic acid at pH 11 was added and the hair completely wetted. The reaction was heated and maintained at 60° C. with stirring for 24 hours. An inert atmosphere of nitrogen was employed during the reaction.

After 24 hours, the liquid fraction was separated from any remaining solids by cannulation under inert atmosphere. Centrifugation under inert atmosphere was employed to effect separation of the liquid and solid fractions in cases where cannulation was difficult. Dissolved keratins were isolated from solution by precipitation via addition of a non-solvent, ethanol, again under inert atmosphere.

The light brown precipitate was separated from the ethanol by filtration and rinsed with additional aliquots of fresh ethanol to remove residual reagents. The resulting keratins were dried overnight under vacuum at room temperature.

Characterization of Water Soluble Keratins

Keratin samples were analyzed for molecular weight by gel permeation chromatography (GPC) analysis. Samples were analyzed on a system employing a Waters model 515 high pressure liquid chromatography (HPLC) pump, Thermo Separation products Model UV100 UV/Vis detector, and Shodex™ GPC column set (OHpak part nos. SB-G, KB-806M, and Q801). The system was calibrated using a set of poly(styrene sulfonate) standards (American Polymer Standards, Inc., Mentor, Ohio). The molecular weights obtained from the samples are shown in Table 1.

TABLE 1

GPC standards data

| Oxidation Time (min.) | Sample ID No. | $M_n$ (g/mole) |
| --- | --- | --- |
| 0 | 1-SEB-31-36 | 133 |
| 30 | 1-SEB-27-36 | 93,338 |
| 60 | 1-SEB-28-36 | 26,807 |
| 120 | 1-SEB-29-36 | 35,218 |
| 180 | 1-SEB-30-36 | 21,633 |

The isoelectric point of each of the samples was also determined. 30 mg of each protein sample was diluted in 300 µL of water. 10 µL of the sample plus 10 µp.L of NOVEX® buffer were loaded onto a NOVEX® pI 3-7 isoelectric focusing (IEF) gel. A molecular weight marker was added and the cathode and anode were diluted with buffer 10:1 and 50:1, respectively. The gel apparatus was assembled and the sample focused for 1.0 hour at 100 volts at room temperature, 1.0 hours at 200 volts at room temperature, and 0.5 hours at 500 volts at room temperature.

EXAMPLE 2

In order to explore the extremes of processing parameters, two different types of water soluble keratins are generated. One type is treated solely oxidatively, and one type is treated solely reductively.

The completely oxidized water soluble keratins are produced using $H_2O_2$ under the conditions described in Example 1. The oxidized keratins contain only sulfonic residues in place of cystine and represent the extreme of a polyionic keratins, under these conditions. The completely oxidized keratins contain no useful functionality resulting from the $H_2O_2$ reaction with cystine. The only opportunity for modification rests with other amino acid residues. The isoelectric point of this type of keratin will be strongly influenced by the polyionic nature of the protein.

The production of completely reduced water soluble keratins presents some challenges. Methods typically employed to reduce cystine residues, such as those described in Example 1, do not result in high yields of the desired product. This is due primarily to the inability of these reagents to break down the cuticle of the hair and penetrate the cortex. Higher pH can be used, but this causes a significant amount of hydrolysis and results in the production of extremely low molecular weight keratins.

In an alternate approach, a first step uses an aggressive reductant, such as sodium sulfide, under conditions effective to break down the cuticle without excess hydrolysis of the cortex. Conditions employed to break down the cuticle without excess hydrolysis of the cortex would be: 1) low concentrations of reductant, typically 1N or less; 2) low reaction temperature, typically 60° C. or less; and 3) shorter reaction times, typically 2 hours or less. The result is a solid fraction that is reduced under mild, controlled conditions, preferably such as those described in Example 1, preferably using thioglycollic acid, mercaptoethanol with or without urea. In the reduced keratins, cystine is completely converted to cysteine, and the reduced keratins represent the extreme of polar keratins, under these conditions.

Soluble keratin peptides produced under these conditions are highly cysteine functional. While the resulting soluble keratin peptides are polar, they do not possess the strong ionic character of the oxidized keratins. These cysteine-rich keratins represent another extreme of isoelectric point.

Combinations of the two techniques result in keratins with intermediate properties. The impact of the techniques on cystine residues are revealed by nuclear magnetic resonance (NMR) spectroscopy. Chemical shift information from alpha and beta $^{13}C$ and $^1H$ reveal the relative ratios of cysteic acid, cystine, and cysteine. These ratios are correlated to the isoelectric point of these samples, and thus demonstrate how the oxidative and reductive treatments affect the solubility characteristics of the resultant soluble keratin peptides.

Persons of ordinary skill in the art will recognize that many modifications may be made to the methods and compositions described in the present application without departing from the spirit and scope of the present application. The embodiment described herein is meant to be illustrative only and should not be taken as limiting the "invention," which is defined in the claims.

What is claimed is:

1. A method for controlling solubility characteristics of a proteinaceous feedstock, said method comprising:
   providing said proteinaceous feedstock comprising primary reactive sites and secondary reactive sites;
   treating said feedstock to convert at least a fraction of said primary reactive sites to an ionic fraction, producing an ionic proteinaceous feedstock; and
   chemically modifying at least a portion of functionalities selected from the group consisting of unreacted primary reactive sites and secondary reactive sites, thereby producing a modified proteinaceous feedstock comprising a polar fraction at a ratio to said ionic fraction; and
   controlling said ratio to achieve solubility characteristics comprising an isoelectric band compatible with a selected solvent.

2. The method of claim 1 wherein said isoelectric band is about 4.5.

3. The method of claim 1 wherein said proteinaceous feedstock is a keratinaceous feedstock.

4. A method for controlling solubility characteristics of a proteinaceous feedstock, said method comprising:
   providing a proteinaceous feedstock comprising primary reactive sites and secondary reactive sites, said primary reactive sites being selected from the group consisting of cystine groups and cysteine groups;
   treating said feedstock to convert at least a fraction of said primary reactive sites to an ionic fraction, producing an ionic proteinaceous feedstock; and
   chemically modifying at least a portion of functionalities selected from the group consisting of unreacted primary reactive sites and secondary reactive sites selected from the group consisting of carboxylic acid groups, amine groups, and hydroxyl groups, thereby producing a modified proteinaceous feedstock comprising a polar fraction at a ratio to said ionic fraction; and
   controlling said ratio to achieve an isoelectric band compatible with a selected solvent.

5. A method for controlling solubility characteristics of a keratinaceous feedstock, said method comprising:
   providing a keratinaceous feedstock comprising primary reactive sites and secondary reactive sites, said primary reactive sites being selected from the group consisting of cystine groups and cysteine groups;
   treating said feedstock to convert at least a fraction of said primary reactive sites to an ionic fraction, producing an ionic keratinaceous feedstock; and
   chemically modifying at least a portion of functionalities selected from the group consisting of unreacted primary reactive sites and secondary reactive sites selected from the group consisting of carboxylic acid groups, amine groups, and hydroxyl groups, thereby producing a modified keratinaceous feedstock comprising a polar fraction at a ratio to said ionic fraction; and controlling said ratio to achieve an isoelectric band compatible with a selected solvent.

6. The method of claim 4 further comprising controlling said ratio to produce said modified keratinaceous feedstock comprising an isoelectric band of about 4.5.

7. The method of claim 5 wherein said modified keratinaceous feedstock comprises modified keratin peptides having a molecular weight of about 15,000 or less.

8. The method of claim 6 wherein said modified keratinaceous feedstock comprises modified keratin peptides having a molecular weight of about 15,000 or less.

9. The method of claim 5 wherein said modified keratinaceous feedstock comprises modified keratin peptides having a molecular weight of about 12,000 or less.

10. The method of claim 6 wherein said modified keratinaceous feedstock comprises modified keratin peptides having a molecular weight of about 12,000 or less.

11. The method of claim 5 wherein said modified keratinaceous feedstock comprises an ionic fraction of amino acid residues comprising oxidized reactive sites and a polar fraction of amino acid residues comprising chemically modified functionalities selected from the group consisting of unoxidized primary reactive sites and secondary reactive sites.

12. The method of claim 5 wherein said modified keratinaceous feedstock comprise an ionic fraction of amino acid residues comprising oxidized reactive sites and a polar fraction of amino acid residues comprising chemically modified functionalities selected from the group consisting of unoxidized primary reactive sites and secondary reactive sites.

13. The method of claim 4 wherein said chemically modifying comprises reacting at least a portion of said functionalities selected from the group consisting of unreacted primary reactive sites and secondary reactive sites with one or more hydrophobic reactant, said method further comprising compatibilizing said hydrophobic reactant with said ionic keratinaceous feedstock.

14. The method of claim 13 wherein said hydrophobic reactant is an organic reactant.

15. The method of claim 5 wherein said chemically modifying comprises reacting at least a portion of said functionalities selected from the group consisting of unreacted primary reactive sites and secondary reactive sites with one or more hydrophobic reactant(s), said method further comprising compatibilizing said one or more hydrophobic reactant(s) with a said ionic keratinaceous feedstock.

16. The method of claim 15 wherein said hydrophobic reactant is an organic reactant.

17. The method of claim 15 wherein said compatibilizing comprises:
providing a first solution comprising said one or more hydrophobic reactant(s) dissolved in a first solvent; and,
mixing said first solution with a second solution comprising said ionic keratinaceous feedstock in a second solvent that is miscible with said first solvent, producing a stable solvent system.

18. The method of claim 17 wherein said first solvent is water-miscible.

19. The method of claim 17 wherein said first solvent is selected from the group consisting of water miscible alcohols, ethers, ketones, sulfones, sulfoxides, and nitrogen-containing solvents.

20. The method of claim 17 wherein said first solvent is selected from the group consisting of methanol, ethanol, propanols, tetrahydrofuran, 1,4-dioxane, acetone, dimethylsulfoxide, amines, and amides.

21. The method of claim 17 wherein said first solvent is selected from the group consisting of water miscible alcohols, ethers, ketones, sulfones, sulfoxides, and nitrogen-containing solvents.

22. The method of claim 17 wherein said first solvent is selected from the group consisting of methanol, ethanol, propanols, tetrahydrofuran, 1,4-dioxane, acetone, dimethylsulfoxide, amines, and amides.

23. The method of claim 17 wherein said first solvent is selected from the group consisting of methanol, ethanol, and propanols.

24. The method of claim 18 wherein said first solvent is selected from the group consisting of methanol, ethanol, and propanols.

25. The method of claim 17 wherein said second solvent is a water-miscible alcohol.

26. The method of claim 18 wherein said second solvent is a water-miscible alcohol.

27. The method of claim 19 wherein said second solvent is a water-miscible alcohol.

28. The method of claim 20 wherein said second solvent is a water-miscible alcohol.

29. The method of claim 24 wherein said second solvent is a water-miscible alcohol.

30. The method of claim 17 wherein said second solvent has a dielectric constant of at least 30.

31. The method of claim 28 wherein said second solvent has a dielectric constant of at least 30.

32. The method of claim 17 wherein said stable solvent system comprises a net dielectric constant sufficiently high to maintain said ionic keratinaceous feedstock in solution and sufficiently low to maintain said one or more hydrophobic reactant(s) in solution.

33. The method of claim 11 wherein said compatibilizing comprises:
providing a first solution comprising said ionic keratinaceous feedstock dissolved in a first solvent; and,
mixing said first solution with a second solution comprising said one or more hydrophobic reactant(s) in a second solvent that is immiscible with said first solvent, said mixing comprising sufficient agitation to create a suspension of said second solvent and said one or more hydrophobic reactant(s) in said second solvent.

34. The method of claim 33 wherein said second solvent has a dielectric constant of 10 or less.

35. The method of claim 33 wherein at least one of said one or more hydrophobic reactant(s) is an organic reactant.

36. The method of claim 11 wherein said compatibilizing comprises:
providing a first solution comprising said one or more hydrophobic reactant(s) dissolved in a first solvent;
mixing said first solution with a second solution comprising said ionic keratinaceous feedstock in a second solvent that is immiscible with said first solvent, said mixing comprising sufficient agitation to create a suspension of said second solvent and said ionic keratinaceous feedstock in said second solvent.

37. The method of claim 36 wherein said first solvent comprises a dielectric constant of 10 or less.

38. The method of claim 36 wherein said first solvent comprises a dielectric constant of less than 10.

39. The method of claim 36 wherein at least one of said one or more hydrophobic reactant(s) is an organic reactant.

40. The method of claim 11 wherein said compatibilizing comprises:
providing a first solution comprising said ionic keratinaceous feedstock dissolved in a first solvent;
providing a second solution comprising said one or more hydrophobic reactant(s) in a second solvent that is immiscible with said first solvent;
providing a surfactant effective to form a stable emulsion comprising said first solution and said second solution; and,
mixing said first solution, said second solution, and said surfactant under conditions effective to form said stable emulsion.

41. The method of claim 40 wherein at least one of said one or more hydrophobic reactant(s) is an organic reactant.

42. The method of claim 11 wherein said compatibilizing comprises:
providing a first solution comprising said ionic keratinaceous feedstock dissolved in a first solvent;
providing a second solution comprising said one or more hydrophobic reactant(s) in a second solvent that is immiscible with said first solvent;
providing a surfactant effective to form a stable emulsion comprising said first solution and said second solution; and, mixing said first solution, said second solution, and said surfactant under conditions effective to form said stable emulsion.

43. The method of claim 42 wherein at least one of said one or more hydrophobic reactant(s) is an organic reactant.

44. Modified protein comprising chemically modified functionalities selected from the group consisting of primary reactive sites and secondary reactive sites comprising a polar fraction at a ratio to an ionic fraction, said polar fraction comprising a hydrophobic reactant and said ionic fraction comprising a hydrophylic component, said hydrophobic reactant and said hydrophilic component comprising other than effective crosslinking agents.

45. Modified keratin peptides comprising chemically modified functionalities selected from the group consisting of primary reactive sites and secondary reactive sites comprising a polar fraction at a ratio to an ionic fraction, said polar fraction comprising a hydrophobic reactant and said ionic fraction comprising a hydrophylic component, said hydrophobic reactant and said hydrophilic component comprising other than effective crosslinking agents.

46. The modified keratin peptides of claim 45 wherein said chemically modified functionalities are selected from the group consisting of thiols; thioethers; products of nucleophilic addition to thiols; and, products of condensation with thiols.

47. The modified keratin peptides of claim 45 wherein said chemically modified functionalities are selected from the group consisting of modified carboxylic acid residues, modified amine residues, and modified hydroxyl residues.

48. The modified keratin peptides of claim 45 wherein said chemically modified carboxylic acid residues are further selected from the group consisting of deprotonated carboxylic acid residues; decarboxylated carboxylic acid residues; reduced carboxylic acid residues; alpha substituted carboxylic acid residues; and nucleophilic acyl substituted carboxylic acid residues.

49. The modified keratin peptides of claim 45 wherein said chemically modified amine residues are selected from the group consisting of alkylated amines, acylated amines, the product of eliminating amines, and the product of addition to amines.

50. The modified keratin peptides of claim 45 wherein chemically modified hydroxyl residues are selected from the group consisting of dehydrated hydroxyl groups, deprotonated hydroxyl groups, oxidized hydroxyl groups, the product of condensation with hydroxyl groups, esterified hydroxyl groups, and alkylated hydroxyl groups.

51. The modified keratin peptides of claim 45 having an isoelectric band of about 4.5.

52. The modified keratin peptides of claim 45 having a molecular weight of about 15,000 or less.

53. The modified keratin peptides of claim 45 having a molecular weight of about 12,000 or less.

54. The modified keratin peptides of claim 46 having a molecular weight of about 15,000 or less.

55. The modified keratin peptides of claim 46 having a molecular weight of about 12,000 or less.

56. The modified keratin peptides of claim 47 having a molecular weight of about 15,000 or less.

57. The modified keratin peptides of claim 47 having a molecular weight of about 12,000 or less.

58. A stable solution comprising a mutual solvent comprising one or more dissolved hydrophobic reactant(s) having a first solubility parameter and ionic proteinaceous feedstock adapted to have a second solubility parameter substantially the same as said first solubility parameter.

59. A stable solution comprising a mutual solvent comprising one or more dissolved hydrophobic reactant(s) having a first solubility parameter and ionic keratin feedstock adapted to have a second solubility parameter substantially the same as said first solubility parameter.

60. The stable solution of claim 59 wherein said ionic keratin feedstock is adapted to maintain an electrical state that is substantially the same as the isoelectric point of said ionic keratinaceous feedstock.

61. The stable solution of claim 59 wherein said mutual solvent comprises a dialectic constant of about 30 or more.

62. A stable solvent system comprising:
ionic proteinaceous feedstock dissolved in a first solvent, said ionic proteinaceous feedstock comprising an ionic fraction; and
one or more hydrophobic reactant(s) dissolved in a second solvent that is miscible with said first solvent.

63. The stable solvent system of claim 62 wherein said first solvent is water.

64. The stable solvent system of claim 62 wherein said second solvent is a water-miscible alcohol.

65. The stable solvent system of claim 62 wherein said second solvent is selected from the group consisting of methanol, ethanol, and propanols.

66. The stable solvent system of claim 62 wherein said second solvents are selected from the group consisting of water miscible alcohols, ethers, ketones, sulfones, and nitrogen-containing solvents.

67. The stable solvent system of claim 62 wherein said second solvents are selected from the group consisting of methanol, ethanol, propanols, tetrahydrofuran, 1,4-dioxane, acetone, dimethylsulfoxide, amines, and amides.

68. The stable solvent system of claim 62 wherein said second solvents are selected from the group consisting of water miscible alcohols, ethers, ketones, sulfones, and nitrogen-containing solvents.

69. The stable solvent system of claim 62 wherein said second solvents are selected from the group consisting of methanol, ethanol, propanols, tetrahydrofuran, 1,4-dioxane, acetone, dimethylsulfoxide, amines, and amides.

70. The stable solvent system of claim 62 comprising a net dielectric constant sufficiently high to maintain said ionic proteinaceous feedstock in solution and sufficiently low to maintain said one or more hydrophobic reactant(s) in solution.

71. A stable solvent system comprising:
   ionic keratinaceous feedstock dissolved in a first solvent, said ionic keratinaceous feedstock comprising an ionic fraction; and,
   one or more hydrophobic reactants dissolved in a second solvent that is miscible with said first solvent.

72. A stable solvent system comprising:
   ionic keratinaceous feedstock dissolved in a first solvent, said ionic keratinaceous feedstock comprising an ionic fraction; and,
   one or more organic reactants dissolved in a second solvent that is miscible with said first solvent.

73. The stable solvent system of claim 72 wherein said first solvent is water.

74. The stable solvent system of claim 72 wherein said second solvent is a water-miscible alcohol.

75. The stable solvent system of claim 73 wherein said second solvent is a water-miscible alcohol.

76. The stable solvent system of claim 72 wherein said second solvent is selected from the group consisting of methanol, ethanol, and propanols.

77. The stable solvent system of claim 72 wherein said second solvents are selected from the group consisting of water miscible alcohols, ethers, ketones, sulfones, and nitrogen-containing solvents.

78. The stable solvent system of claim 72 wherein said second solvents are selected from the group consisting of methanol, ethanol, propanols, tetrahydrofuran, 1,4-dioxane, acetone, dimethylsulfoxide, amines, and amides.

79. The stable solvent system of claim 72 wherein said second solvents are selected from the group consisting of water miscible alcohols, ethers, ketones, sulfones, and nitrogen-containing solvents.

80. The stable solvent system of claim 72 wherein said second solvents are selected from the group consisting of methanol, ethanol, propanols, tetrahydrofuran, 1,4-dioxane, acetone, dimethylsulfoxide, amines, and amides.

81. The stable solvent system of claim 72 comprising a net dielectric constant sufficiently high to maintain said ionic keratin feedstock in solution and sufficiently low to maintain said one or more hydrophobic reactant(s) in solution.

82. A stable suspension comprising one or more hydrophobic reactant(s) comprising a second solvent suspended in a first solvent comprising ionic proteinaceous feedstock comprising an ionic fraction, wherein said second solvent is immiscible with said first solvent.

83. The stable suspension of claim 82 wherein said second solvent has a dielectric constant of 10 or less.

84. A stable suspension comprising an ionic keratinaceous feedstock suspended a first solvent, said stable suspension further comprising one or more dissolved hydrophobic reactant(s) comprising a second solvent, wherein said first solvent is immiscible with said second solvent.

85. The stable suspension of claim 83 wherein said first solvent has a dielectric constant of 10 or less.

86. A stable emulsion comprising one or more hydrophobic reactant(s)0 dissolved in a first solvent and emulsified droplets comprising ionic proteinaceous feedstock comprising an ionic fraction in a second solvent that is immiscible with said first solvent.

87. The stable emulsion of claim 86 wherein said first solvent has a dielectric constant of 10 or less.

88. The stable emulsion of claim 86 further comprising surfactant effective to stabilize said emulsion.

89. A stable emulsion comprising ionic proteinaceous feedstock comprising an ionic fraction dissolved in a first solvent and emulsified droplets comprising one or more hydrophobic reactant(s) in a second solvent that is immiscible with said first solvent.

90. The stable emulsion of claim 89 wherein said second solvent has a dielectric constant of 10 or less.

91. The stable emulsion of claim 89 further comprising surfactant effective to stabilize said emulsion.

92. A stable emulsion comprising one or more hydrophobic reactant(s) dissolved in a first solvent and emulsified droplets comprising ionic keratinaceous feedstock comprising an ionic fraction in a second solvent that is immiscible with said first solvent.

93. The stable emulsion of claim 92 wherein said first solvent has a dielectric constant of 10 or less.

94. The stable emulsion of claim 92 further comprising surfactant effective to stabilize said emulsion.

95. A stable emulsion comprising ionic keratinaceous feedstock comprising an ionic fraction dissolved in a first solvent and emulsified droplets comprising one or more hydrophobic reactant(s) in a second solvent that is immiscible with said first solvent.

96. The stable emulsion of claim 95 wherein said second solvent has a dielectric constant of 10 or less.

97. The stable emulsion of claim 95 further comprising surfactant effective to stabilize said emulsion.

* * * * *

UNITED STATES PATENT AND TRADEMARK OFFICE
CERTIFICATE OF CORRECTION

PATENT NO. : 7,001,988 B2
DATED : February 21, 2006
INVENTOR(S) : Mark Van Dyke

It is certified that error appears in the above-identified patent and that said Letters Patent is hereby corrected as shown below:

Column 36,
Line 14, delete "reactant(s)0" and insert -- reactant(s) --.

Signed and Sealed this

Twenty-fifth Day of April, 2006

JON W. DUDAS
*Director of the United States Patent and Trademark Office*